United States Patent
Holmberg et al.

(10) Patent No.: US 7,018,404 B2
(45) Date of Patent: Mar. 28, 2006

(54) CONDUIT FOR AORTA OR PULMONARY ARTERY REPLACEMENT

(75) Inventors: William R. Holmberg, New Richmond, WI (US); Mario Osvaldo Vrandecic Peredo, Belo Horizonte (BR)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 10/056,774

(22) Filed: Jan. 24, 2002

(65) Prior Publication Data

US 2003/0139805 A1  Jul. 24, 2003

(51) Int. Cl.
*A61F 2/06* (2006.01)

(52) U.S. Cl. .................. 623/1.26; 623/1.32; 623/2.15; 623/2.19; 623/2.22

(58) Field of Classification Search .............. 623/1.24, 623/1.26, 2.1, 900, 2.2, 2.21, 2.22, 2.23, 623/2.24, 2.25, 2.26, 2.27, 2.28, 2.29, 2.3, 623/2.31, 2.32, 2.33, 1.13, 1.32
See application file for complete search history.

(56) References Cited

U.S. PATENT DOCUMENTS

| | | | | |
|---|---|---|---|---|
| 4,086,665 A | * | 5/1978 | Poirier | 623/1.44 |
| 4,313,231 A | * | 2/1982 | Koyamada | 623/1.32 |
| 5,139,515 A | | 8/1992 | Robicsek | |
| 5,314,468 A | | 5/1994 | Martinez | |
| 5,376,112 A | | 12/1994 | Duran | |
| 5,545,215 A | * | 8/1996 | Duran | 623/1.26 |
| 5,824,037 A | * | 10/1998 | Fogarty et al. | 623/1.13 |
| 5,891,195 A | * | 4/1999 | Klostermeyer et al. | 623/1.26 |
| 6,068,657 A | * | 5/2000 | Lapeyre et al. | 623/2.2 |
| 6,197,143 B1 | | 3/2001 | Bodnar | |
| 6,264,691 B1 | | 7/2001 | Gabbay | |
| 6,352,554 B1 | * | 3/2002 | De Paulis | 623/1.26 |
| 6,544,285 B1 | * | 4/2003 | Thubrikar et al. | 623/2.12 |
| 2001/0041927 A1 | * | 11/2001 | Solem | 623/1.13 |
| 2001/0049553 A1 | * | 12/2001 | De Paulis | 623/1.24 |

FOREIGN PATENT DOCUMENTS

WO   WO 01/52776 A1   7/2001
WO   WO 02/053069 A2  7/2002

* cited by examiner

*Primary Examiner*—Corrine McDermott
*Assistant Examiner*—Thomas J. Sweet
(74) *Attorney, Agent, or Firm*—Westman, Champlin & Kelly, P.A.; Hallie A. Finucane

(57) ABSTRACT

Prosthetic conduits include biocompatible material formed into a generally cylindrical section and an expanded section connected to the generally cylindrical section. The conduit has a lumen extending through the generally cylindrical section and the expanded section. The biocompatible material may be tissue. The biocompatible material can include one segment or a plurality of segments joined together to form the generally cylindrical section and the expanded section. The prosthetic conduit may include a reinforcement to prevent dilation or collapse of the conduit. The reinforcement can be placed at or near the junction of a generally cylindrical section and an expanded section and/or at other locations along the conduit. The prosthetic conduit may include a prosthetic heart valve. The prosthetic conduit can include tubules to facilitate attachment of coronary arteries to the prosthetic conduit The prosthetic conduit includes two sections that are joined to form the prosthetic conduit.

51 Claims, 11 Drawing Sheets

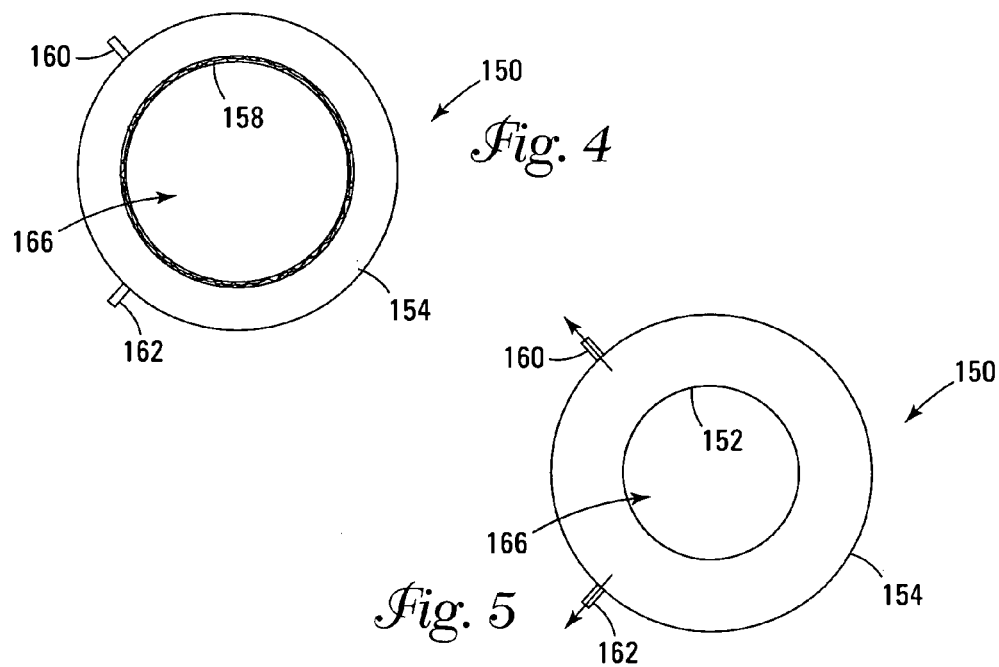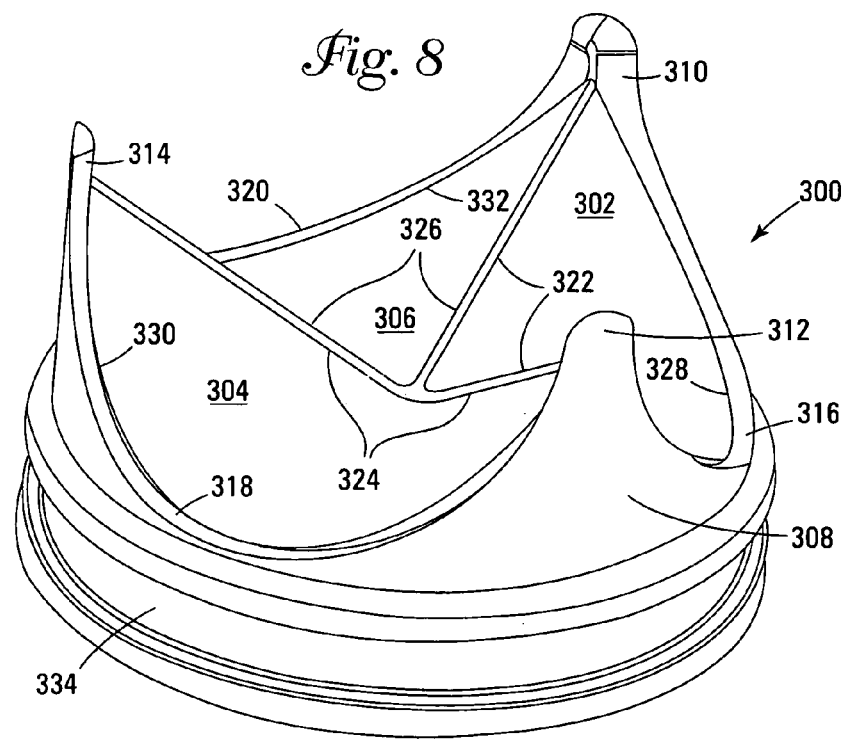

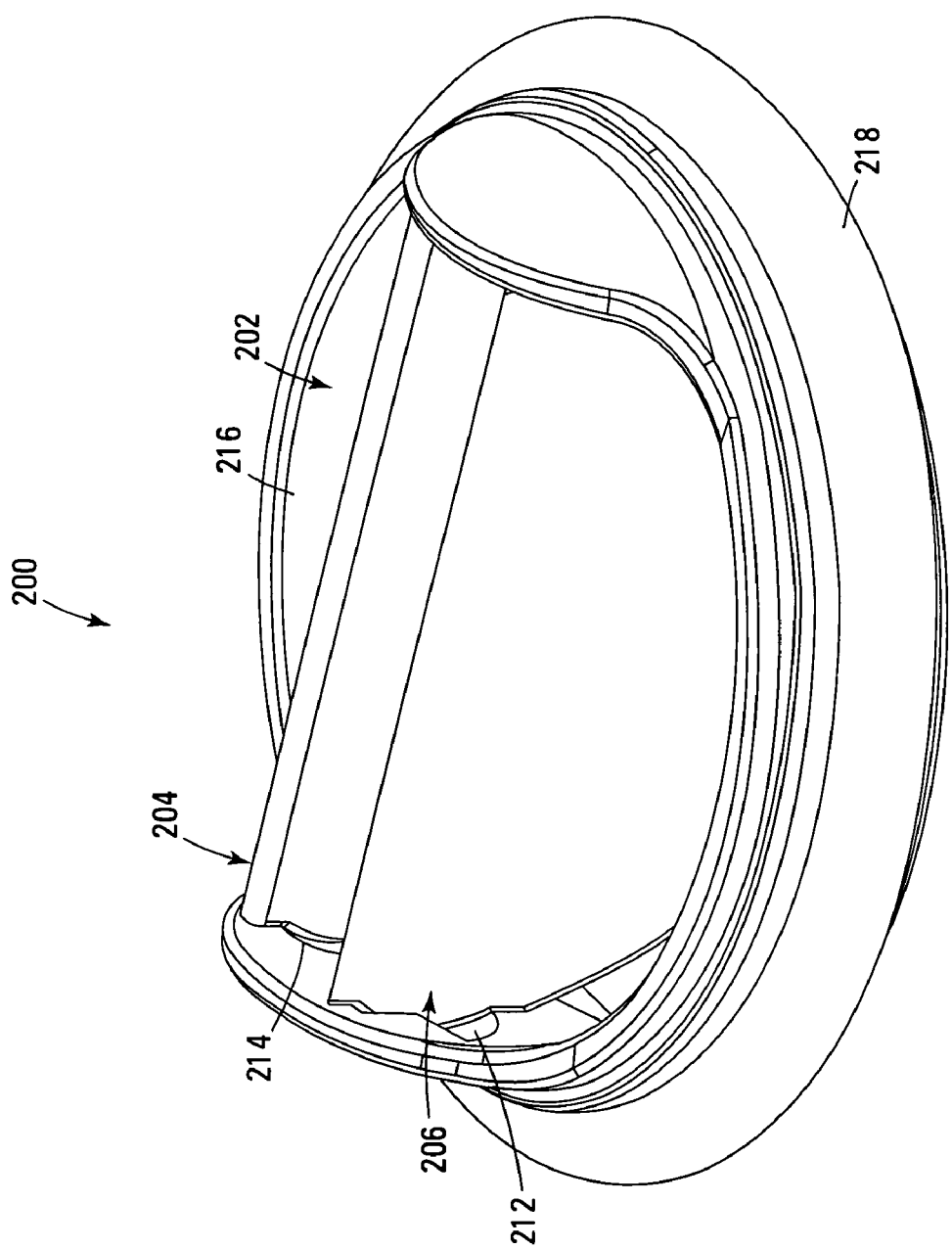

CONDUIT FOR AORTA OR PULMONARY ARTERY REPLACEMENT

FIELD OF THE INVENTION

The invention relates to prostheses for the replacement of blood vessels and, optionally, valve, especially at or near a heart valve. More specifically, the invention relates to prostheses for aorta or pulmonary artery replacement, particularly at, adjacent and/or proximal the respective aortic or pulmonary heart valve. The prostheses may include a valve, such as a heart valve.

BACKGROUND OF THE INVENTION

Physicians use a variety of prostheses to correct problems associated with the cardiovascular system, especially the heart. For example, the ability to replace or repair diseased heart valves with prosthetic devices has provided surgeons with a method of treating heart valve deficiencies due to disease and congenital defects. A typical procedure involves removal of the native valve and surgical replacement with a prosthetic heart valve.

Prosthetic heart valve leaflets or occluders perform the function of opening and closing to regulate the blood flow through the heart valve. Typically, heart valve leaflets must either pivot or flex with each cycle of the heart to open and close the valve. Heart valves function as check valves, which open for flow in one direction and close in response to pressure differentials to limit reverse flow.

Aortic and pulmonary heart valves are positioned at the connection of arteries to the left and right heart ventricles, respectively. Replacement or repair of these valves may involve disconnecting and reconnecting the corresponding artery. This process can involve the replacement of a portion of the artery adjacent the valve with a prosthetic conduit. In addition, it may be desirable to replace the portion of the artery adjacent the valve due to degeneration of the artery even if there is no damage to the valve. Whether or not the heart valve is replaced along with the portion of the artery adjacent the heart valve, the procedure for replacing the artery should not interfere with valve function.

Both the natural aorta and the pulmonary artery have slightly dilated portions adjacent the heart valves called Sinuses of Valsalva. The natural sinuses of the aorta are somewhat larger than the sinuses of the pulmonary artery. The aorta adjacent the aortic heart valve is connected to coronary arteries that provide aerated blood to the heart muscle. Replacement of this portion of the aorta involves reconnection of the coronary arteries.

SUMMARY OF THE INVENTION

In a first aspect, the invention pertains to a prosthesis including a reinforcement element and a prosthetic conduit including biocompatible material. The prosthetic conduit includes a generally cylindrical section and an expanded section extending from the generally cylindrical section. Generally, the reinforcement element overlaps the junction between the generally cylindrical section and the expanded section. In some embodiments, the prosthetic conduit also has a reinforcement at the inflow edge and/or the outflow edge.

In another aspect, the invention pertains to a prosthesis including biocompatible material formed into a generally cylindrical section and an expanded section extending from the generally cylindrical section. The expanded section includes tubules connecting the central lumen of the expanded section to an external opening.

In an additional aspect, the invention pertains to a prosthesis comprising biocompatible material formed into a generally cylindrical section and an expanded section connected to the generally cylindrical section, forming a conduit. The conduit has a lumen extending through the generally cylindrical section and the expanded section. The biocompatible material can be a single segment or a plurality of segments that are joined to form the conduit. The free edge of the expanded section has scallops that fit adjacent to and downstream from the commissures of a native heart valve.

In a further aspect, the invention pertains to a prosthesis including a reinforcement element, a prosthetic conduit comprising biocompatible material and a prosthetic valve. The reinforcement element is attached to the prosthetic conduit downstream from the prosthetic valve to inhibit dilation of the conduit and promote proper function of the valve.

Furthermore, the invention pertains to a prosthetic system comprising a first prosthetic conduit section and a second prosthetic conduit section. The inflow edge of the first prosthetic conduit section is configured for attachment to the outflow edge of the second prosthetic conduit section. The first prosthetic conduit section has a generally cylindrical section, and the second prosthetic conduit section includes a prosthetic valve.

In addition, the invention pertains to a prosthesis comprising a reinforcement element and a prosthetic conduit. The prosthetic conduit comprises biocompatible material. The prosthesis can further comprise a prosthetic valve in some embodiments. The reinforcement element is attached to the prosthetic conduit proximate to the outflow edge.

In an additional aspect, the invention pertains to a prosthesis comprising a reinforcement element, a prosthetic conduit comprising biocompatible material and a prosthetic valve attached to the prosthetic conduit. The reinforcement element is attached to the prosthetic conduit proximate to the inflow edge.

BRIEF DESCRIPTION OF THE DRAWINGS

FIG. 4 is an end view of the biological conduit of FIG. 3.

FIG. 5 is a sectional view of the biological conduit of FIG. 3 taken along line 5—5 of FIG. 3.

FIG. 6 is a perspective view of a mechanical heart valve prosthesis.

FIG. 8 is a perspective view of a stented heart valve prosthesis with flexible leaflets.

DETAILED DESCRIPTION OF THE INVENTION

Figure 1:
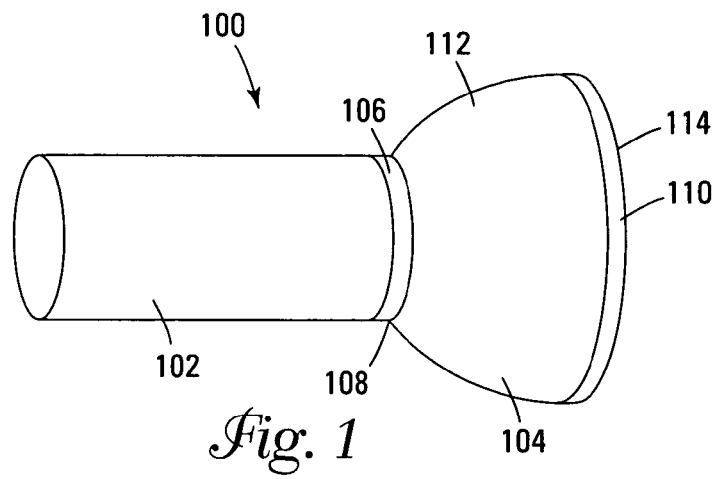
FIG. 1 is a side perspective view of a biological conduit with an expanded section corresponding to sinuses of Valsalva.

Improved prosthetic conduits may include structures with an expanded section at locations corresponding with sinus structures of arteries near the attachment to the heart. The expanded section reflects the expanded character of the natural sinuses, but may or may not have a similar shape as the natural sinuses. The inclusion of the expanded section is particularly appropriate when the native sinuses are removed. To maintain proper coaptation of the valve, the prosthetic conduit can include a reinforcement between the expanded section and an adjacent unexpanded section to inhibit unwanted dilation at the intersection of the two sections, such that the coaptation of the leaflets is maintained. Similarly, reinforcements can be located at the inflow edge to help to maintain valve function. Reinforcements can be advantageously used adjacent prosthetic valves even in embodiments in which the prosthetic conduit does not have an expanded section, for example, if the native sinuses are not removed. The presence of an expanded section analogous to the natural sinuses facilitates the reattachment of the coronary arteries to an aortic prosthesis. In additional embodiments, the conduit includes specific structure that provides for simplified attachment of the coronary arteries to the conduit. In general, the improved prosthetic conduits, especially those with reinforcements, can be particularly advantageous when native heart valves are replaced with prosthetic valves without a stent. The conduit may or may not include a heart valve as part of the conduit.

Damaged or diseased natural heart valves can be replaced with prosthetic valves to restore valve function. The aortic heart valve and the pulmonary heart valve are located at the points of connection between the heart and arteries, the aorta and the pulmonary artery, respectively. During the replacement of the aortic heart valve and/or the pulmonary heart valve, a portion of prosthetic conduit can be used to replace a portion of the respective arteries. Furthermore, a portion of the arteries can be replaced as part of a procedure to repair the heart valves. In addition, a portion of the arteries can be replaced adjacent the heart due to disease or damage of the artery to reconstruct the artery without repairing or replacing the valve. The patient can be an animal, especially a mammal, and preferably is a human.

Mechanical heart valve prostheses can have leaflets formed from a rigid material that pivot to open and close the valve. Mechanical valves generally have an orifice ring that forms the valve lumen with one or more leaflets attached to the orifice ring. Alternatively, the heart valve prostheses can have flexible leaflets that flex to open and close the valves. Flexible leaflets can be formed from tissue or flexible polymers.

In a prosthetic valve with flexible leaflets, the leaflets are supported by a support structure that includes commissure supports and scallops between the commissure supports. In some embodiments, the support structure includes a rigid component that maintains the leaflet function of the valve against the forces opening and closing the valve. Valves with a rigid support structure are termed stented valves, and the rigid support is called a stent. The stent provides a scaffolding for the leaflets. The stent generally is sufficiently rigid such that only the base of the stent is attached to the patient or other device.

In alternative embodiments, the support structure is not sufficiently rigid to maintain the leaflet function of the valve against the forces opening and closing the valve. In these embodiments, the valve is termed stentless. In a stentless valve, the support structure also has commissure supports at which the free edge of the leaflets connect with the support structure, and scallops which support the attached edge of the leaflets. However, in the stentless valve, the support structure is less rigid such that both edges of the support structure, i.e., the inflow edge and the outflow edge, must be secured, such as by suturing or other fastening approach, to other anatomical structures, such as the wall of a blood vessel, or to other device structures, such as a prosthetic conduit, to prevent the valve from collapsing against the fluid pressure. The prosthesis, especially a stentless prosthesis, can also have scallops along the inflow edge to approximately match the native annulus following removal of the native leaflets.

Regardless of the particular design, valve leaflets are configured to open and close in response to changes in blood flow. In particular, the leaflets function as one way check valves that open to allow flow in a desired direction and close in response to pressure differentials to limit reverse flow. Thus, when blood is flowing downstream, the leaflets fully open to allow for flow through the valve. The leaflets correspondingly close to inhibit flow upstream. For the aortic and pulmonary valves, the valves open for flow from the heart into the arteries and close to resist flow back from the arteries into the heart.

The conduit prostheses described herein can be used for the replacement of the aorta adjacent the heart or the pulmonary artery adjacent the heart. Prostheses for replacement of the pulmonary artery do not attach to coronary arteries or the equivalent thereof. Thus, the prostheses for the replacement of pulmonary arteries are correspondingly simpler than the prostheses for the replacement of the section of the aorta.

The aorta and pulmonary artery have a small dilated section with three sinuses adjacent the attachment site to the heart. The dilated sections of the aorta and pulmonary artery are termed the sinuses of Valsalva. The sinuses extend between the commissures of the valve. Thus, the native valve is located within the sinuses section of the artery. The sinuses provide space for the opening of the leaflets and, in the case of the aorta, for attachment of the coronary arteries. Downstream, the sinuses connect to an undialated portion of the respective arteries, the pulmonary artery or the ascending aorta.

For the aorta, two coronary arteries, the left coronary artery and the right coronary artery, attach to the sinuses. These arteries provide the blood flow to the heart muscle. Sufficient blood flow to the heart muscle is necessary for heart function. In a native aorta, the coronary arteries are positioned to avoid the natural commissures supporting the native leaflets of a native aortic valve. Replacement of the valve and/or the adjacent section of the aorta should provide for maintaining flow from the aorta into the coronary arteries.

In embodiments of particular interest, the prosthetic conduit includes an expanded section corresponding to the location of the natural sinuses of Valsalva. The prosthetic conduit further includes a generally cylindrical section extending from the expanded section. In some embodiments, a reinforcement is placed at or near the connection between the expanded section and the generally cylindrical section. The presence of the expanded section can provide for structure near the heart valve that is more similar to native structure and function.

A reinforcement, in general, can prevent undesirable dilation whether or not the prosthetic conduit includes an expanded section. Suitable reinforcements generally are positioned at the inflow edge, downstream from the valve at the top of commissure supports and/or at the outflow edge. If an expanded section is present, a downstream reinforcement generally is placed at or near the junction of the expanded section and the generally cylindrical section. To provide an appropriate level of reinforcement, the reinforcement generally encircles the circumference of the prosthetic conduit, although the reinforcement can encircle a significant fraction of the circumference with one or several disconnected sections rather than the entire circumference.

Replacement of the aorta or pulmonary artery or portions thereof may also involve replacement of the heart valve. If the heart valve is also replaced, the valve and section of aorta or pulmonary artery can be replaced as a single unit or as two components. Mechanical prosthetic valves generally have a low profile such that the orientation of the valve with respect to the coronary arteries is not significant. However, valves with flexible leaflets have a higher profile such that the support structure has to be positioned with the commissure supports oriented to avoid blocking the coronary arteries. The structure of the prosthetic conduit can be designed to facilitate orientation of the prosthetic valve by including structure and/or markings that indicate the valve orientation within the prosthesis.

The coronary arteries may or may not be disconnected from the aorta when a section of aorta near the heart, i.e., the ascending aorta, is removed for replacement. Specifically, the aorta can be severed along the sinuses, leaving the coronary arteries intact along a portion of the sinuses at the attachment to the native heart valve. The prosthetic conduit can be shaped to attach to the remaining portion of the sinuses while avoiding the coronary arteries. Alternatively, the aorta can be severed along the scallops of the valve such that the coronary arteries are disconnected from the valve. In further embodiments, the prosthetic conduit can replace the entire aorta adjacent the heart such that the coronary arteries are attached to the conduit. The presence of the expanded section facilitates attachment of the prosthetic conduit in the aortic position with the coronary arteries. Since the coronary arteries are positioned for attachment to the natural sinuses, the presence of prosthetic sinuses can involve reattachments taking into account the natural positioning of the coronary arteries.

If the corresponding heart valve is not replaced, the end of the prosthetic conduit can be shaped to attach to the section of the sinuses that is not removed. For the aorta, the expanded section of the prosthesis should be attached to account for the presence of the coronary arteries. Even though the aorta can be cut along the sinuses while leaving the coronary arteries intact, it may be desirable to cut the sinuses along the scallops of the valve, in which case, the coronary arteries would be disconnected from the remaining sections of the aorta.

In other embodiments, the heart valve prosthesis is replaced along with a portion of the artery while leaving the natural sinuses or a portion thereof intact. For the aorta, the prosthetic valve can be implanted following removal of the native leaflets while leaving the coronary arteries and the corresponding section of the aorta intact. In these embodiments, the section of the prosthetic conduit can have the same conduit structure with an expanded section as the embodiments in which the aortic heart valve is not replaced. The heart valve can be replaced with a prosthetic valve with flexible leaflets that is parachuted down the remaining section of artery. The aortic valve is positioned with the proper location and orientation relative to the attached coronary arteries.

In additional embodiments, the entire artery adjacent the heart is removed. The native heart valve is also removed and replaced with a prosthetic valve. In these embodiments, for the aorta, the coronary arteries are attached to the prosthetic conduit. If the prosthetic valve is a mechanical valve with a typical low profile, the orientation of the valve relative to the placement of the coronary arteries generally is not as important since the coronary arteries are generally connected to the conduit far enough away from the valve that the valve structure does not block flow into the coronary arteries. If the orientation of the mechanical valve is significant, the valve can be oriented with markings, as appropriate, to guide the implantation. For prosthetic aortic valves with flexible leaflets, the orientation of the valve is significant to avoid blocking flow into the coronary arteries with the commissure supports.

If the portion of artery adjacent the heart is replaced along with the corresponding heart valve, the prosthesis can be formed as a single unit with the valve attached to the conduit. This single unit should provide for the attachment of the coronary arteries. In some of these embodiments, generally embodiments with mechanical valves, the coronary arteries can be attached at selected locations during implantation by the surgeon by forming small holes in the conduit and connecting the arteries to an appropriately placed hole. The conduit can include markings to facilitate orientation of the conduit and valve as well as for proper placement of the coronary arteries for the aorta. Alternatively, the conduit can include tubules that extend from the conduit for attachment of the coronary arteries. Since the prosthesis is formed as a unit, the tubules can be positioned during assembly to avoid the support structure of the leaflets as well as for appropriate positioning for the attachment of the coronary arteries. The prosthesis can be oriented for implantation by orienting the tubules for convenient attachment of the coronary arteries.

In alternative embodiments, the prosthesis includes two components that interconnect to complete the replacement of the removed native tissue. One interconnecting component of the complete prosthesis, the conduit component, is a prosthetic conduit. The second interconnecting component, the valved component, includes the prosthetic heart valve along with the portion of the prosthetic conduit surrounding the valve. Since the component is formed with the valve already attached to the portion of conduit, the implantation involves attachment of the valved component to the heart. The interconnecting components generally are designed to provide for the attachment of the coronary arteries, especially for prosthetic valves with flexible leaflets. For example, the coronary arteries can be attached to appropriately placed holes in the side of the conduit between the commissure supports. Alternatively, the conduit can include tubules for the attachment of the coronary arteries. The conduit component and the valved component fit together to complete the prosthesis with appropriate orientation of the components to account for the positioning and attachment of the coronary arteries.

Approaches used to form the various components can be selected based on the type of material being used. Specifically, tissue components can be assembled from sections of tissue to have the particular shape. Sheets of tissue or other biocompatible material can be shaped and fastened in a particular tubular form of the conduit structure. The prosthetic heart valves generally can be formed separately and then attached to a conduit section, if appropriate, when the conduit section is being shaped into the tubular form. Alternatively, the valve components can be assembled as an integral part of the conduit when forming the overall prosthesis.

Having an expanded portion in the conduit provides for functioning of the heart valve more similarly to the native structure than with prosthetic conduits without an expanded section. Natural sinuses can provide an increased valve lumen and pressure differentiation at the valve. For the aorta, the expanded portion simplifies the attachment of the coronary arteries since the expanded portion extends outward to mimic native sinuses. In contrast, in embodiments without the expanded portion, the coronary arteries are positioned to compensate for the extra distance to a generally cylindrical conduit section. A reinforcement at appropriate positions along the prosthetic conduit can prevent or limit the expansion of the prosthetic conduit and the corresponding deformation of the valve.

In embodiments with a prosthetic valve, the prosthesis can provide for simplified attachment of both the valve and the conduit. In particular, the prostheses are designed for convenient attachment of the coronary arteries while simultaneously accounting for the positioning of commissure supports for valves with flexible leaflets. If the portion of the aorta adjacent the heart is replaced, forms of attachment along the expanded section to tubules or to holes in the conduit can be used to facilitate reattachment of the coronary arteries without interference from the support structure of the valve, especially if the valve has flexible leaflets. Due to these improved features, the surgical times can be reduced so that the patient's time on a by-pass machine can be correspondingly reduced.

Prosthetic Conduits

The prostheses described herein generally include a prosthetic conduit for the replacement of a portion of the aorta or the pulmonary artery adjacent or near the heart. The prostheses may or may not include a prosthetic valve. Prostheses that include a prosthetic valve are described further below. Prosthetic conduits can be used when the heart valve is separately replaced with a portion of the aorta or pulmonary artery adjacent the valve remaining intact. In preferred embodiments, the prosthetic conduit has an expanded section corresponding to the sinuses of the native aorta or pulmonary artery. However, some of the features for attachment of coronary arteries can be incorporated into improved prosthetic conduits without an expanded section. In some embodiments, the conduit includes tubules for the attachment of the coronary arteries to the conduit to provide fluid communication between the interior of the conduit and the coronary arteries.

Referring to FIG. 1, an embodiment of a prosthetic conduit is shown. Prosthetic conduit 100 includes a generally cylindrical section 102 and an expanded section 104. In some embodiments, prosthetic conduit 100 has an optional reinforcement 106 at or near junction 108 of cylindrical section 102 and expanded section 104. Prosthetic conduit 100 can optionally include a sewing ring 110 and/or a reinforcement. In general in the embodiments herein, sewing rings may or may not be included at the inflow and outflow edges of the prosthetic conduits. If formed appropriately, the sewing ring may also provide reinforcement of the prosthetic conduit. However, the sewing ring may not be present, or the sewing ring may not provide significant reinforcement of the conduit. Thus, a separate reinforcement with the properties described herein can be added at the outflow and/or inflow edges of the conduit, optionally along with reinforcements in other locations along the conduit, such as optional reinforcement 106 of FIG. 1.

Prosthetic conduits generally can be formed in a range of sizes to accommodate a particular patient. For example, the prosthetic conduit could be produced in a series of sizes, such as six sizes or more than six sizes, such that the physician can select one of the sizes for implantation. Pulmonary prosthetic conduits are on average smaller than aortic prosthetic conduits. The diameter of the generally cylindrical section typically would vary according to the natural geometry of the patient. For most patients, the average diameter of the generally cylindrical section of an aortic prosthetic conduit would range from about 20 millimeters (mm) to about 40 millimeters, and in further embodiments, from about 20 mm to about 35 mm. Similarly, the average diameter of the generally cylindrical section of a pulmonic prosthetic conduit would range from about 8 mm to about 30 mm, and in further embodiments, from about 12 mm to about 24 mm. While generally cylindrical section 102 has a generally cylindrical shape, it may be slightly tapered and/or slightly irregular in shape. However, the diameter of generally cylindrical section 102 generally varies along its length by no more than about eight percent from the average diameter, in other embodiments, by no more than about five percent from the average diameter, and in further embodiments, by no more than about three percent from the average diameter. A person of ordinary skill in the art will recognize that additional ranges between these particular ranges are contemplated and are within the present disclosure.

In contrast with the generally straight surface along the axial direction of the generally cylindrical section, the expanded section 104 generally has a curved surface along the flow direction. The curved surface can have a sinus shape, a partial spherical shape or other convenient shape. The structure of the valve may influence the shape of the expanded section. For example, in embodiments in which the native valve is maintained, scalloped edges of the expanded section attach to the native structure and the expansion about the attachment edge may naturally form some lobed-type configuration, although the lobes may have different shapes from natural sinuses. Expanded section 104 generally increases in diameter along curved surface 112 with distance from junction 108 and may reach a maximum diameter such that the diameter then decreases toward inflow edge 114. In general, the maximum diameter of expanded section 104 is at least about 10% larger than the average diameter of the generally cylindrical section 102, in other embodiments at least about 12% larger, in further embodiments at least about 15% larger, and in still other embodiments, about 20% larger than the average diameter of the generally cylindrical section. A person of ordinary skill in the art will recognize that additional ranges within the explicit ranges above are contemplated and are within the present disclosure. Optional reinforcement 106 resists or prevents dilation of the conduit along generally cylindrical section 102.

Generally, reinforcements anywhere along the prosthetic conduit, such as reinforcement 106, is a section of material separate from the prosthetic conduit, although a reinforcement can be a rolled up section of the material of the prosthetic conduit that is then attached to the prosthetic conduit to complete the formation of the prosthetic conduit. Reinforcements generally encircle the circumference of prosthetic conduit, although the reinforcement can encircle a significant portion of the circumference in alternative embodiments. Reinforcements can have various shapes consistent with the location along the circumference of the prosthetic conduit. In particular, the reinforcement can have various shapes, such as a ring, a band shape, an irregular shape or other shape that encircles the conduit as desired. Reinforcements can be radio-opaque for imaging purposes. The thickness of a reinforcement generally depends on the material used to form the reinforcement. In general, a reinforcement has a thickness from about 0.1 mm to about 3 mm, and in other embodiments, from about 0.2 mm to about 2 mm.

While embodiments of particular interest have an expanded section, reinforcements can be useful to prevent dilation of other prosthetic conduits without an expanded section. In particular, reinforcements can be effective to prevent dilation of a prosthetic conduit adjacent a valve to maintain proper coaptation of the valve. Prosthetic conduits adjacent a valve tend to be subjected to dilation due to forces from the valve function and pressure increases upon valve opening. The valve can be a mechanical valve or a prosthetic valve with flexible leaflets. Generally, the reinforcement is placed within about 2 centimeters (cm) from the downstream edge of the prosthetic valve, in other embodiments within about 1 cm, and in further embodiments, within about 0.5 cm from the downstream edge of the prosthetic valve. The placement of the reinforcement can be influenced by the particular type of valve. Larger distances may be appropriate for embodiments with a mechanical valve or a stented valve, and shorter distances may be appropriate for embodiments with a stentless valve or for conduits without valves.

Figure 2:
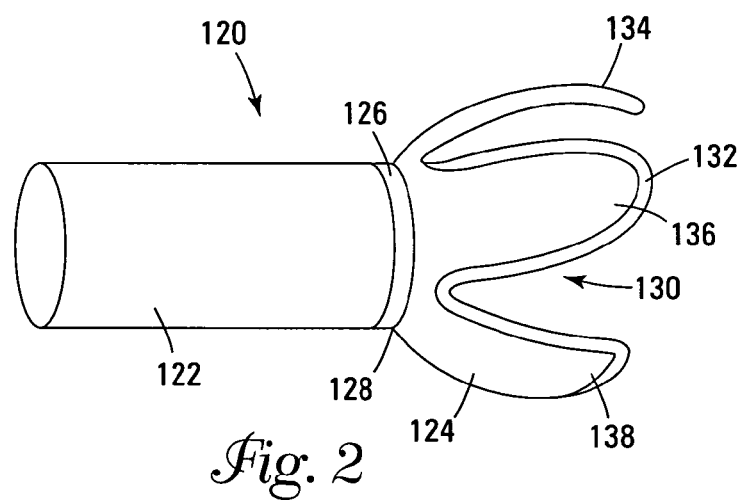
FIG. 2 is a side perspective view of a biological conduit with an expanded section with a scalloped edge.

In some embodiments, the inflow edge of the prosthetic conduit is shaped to facilitate attachment of the conduit to native anatomy. Referring to FIG. 2, prosthetic conduit 120 has a generally cylindrical section 122, an expanded section 124, and a reinforcement 126 at junction 128 between generally cylindrical section 122 and expanded section 124. Inflow edge 130 has an optional sewing ring 132 and/or reinforcement. While prosthetic conduit 100 of FIG. 1 has an approximately planar inflow edge 114, prosthetic conduit 120 of FIG. 2 has a shaped inflow edge 130. As shown in FIG. 2, inflow edge 130 has a scallop shape with three sinuses 134, 136, 138. The sinuses of this embodiment can be generally analogous to native sinuses. The scalloped inflow edge is suitable for attachment to a native valve in which the scallops of the conduit fit between and attach to the scallops and commissures of the native valve support. During implantation, the coronary arteries can be attached along two of sinuses 134, 136, 138 that are aligned for attachment of the arteries. Holes can be formed in the sinuses, with a punch, scissors, scalpel or the like, for the attachment of the coronary arteries. Similarly, sinuses 134, 136, 138 can be positioned between commissures of a prosthetic valve with flexible leaflets. Attachment of prosthetic conduit 120 along sewing ring 132 provides a secure attachment while reducing the risk of piercing a leaflet during implantation. As an alternative to the use of a sewing ring, the edge can be trimmed to match the native anatomy such that the edge can be directly attached to the native structure. Other shapes of the inflow edge can be used to facilitate attachment for a particular situation. For example, a particular shape of the inflow edge can be used with a separate prosthetic valve component to facilitate implantation and joining of the two components of the prosthesis.

Figure 3:
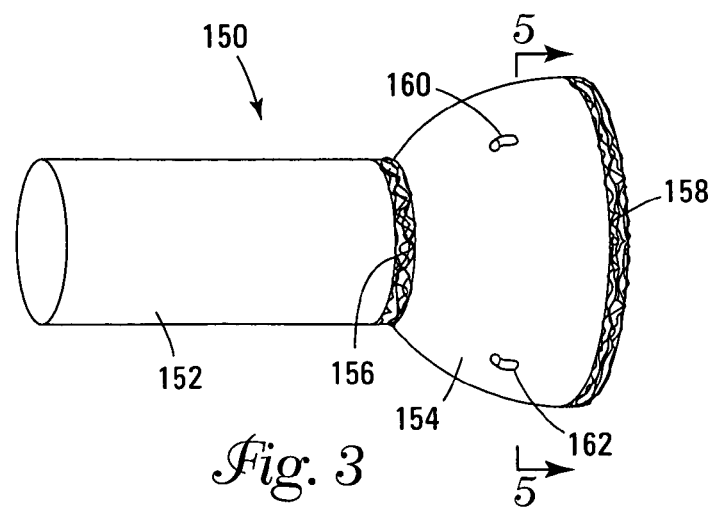
FIG. 3 is a side perspective view of a biological conduit with an expanded section with tubules for the attachment of coronary arteries.

In other alternative embodiments, the prosthetic conduit includes tubules for the attachment of the coronary arteries. Referring to FIGS. 3–5, prosthetic conduit 150 includes a generally tubular section 152, an expanded section 154, a reinforcement 156 and an optional sewing ring 158 and/or inflow edge reinforcement. Tubules 160, 162 extend from expanded section 154 for the attachment of the right and left coronary arteries. Referring to FIG. 5, tubules 160, 162 provide for fluid flow from the interior 166 of expanded section 154 through the tubules, as noted with the arrows in FIG. 5.

Prosthetic conduits can be formed from natural materials, synthetic materials or combinations thereof. Suitable natural materials include, for example, tissue. Appropriate bioprosthetic tissue materials can be formed from natural tissues, synthetic tissue matrices and combinations thereof. Synthetic tissue matrices can be formed from extracellular matrix proteins that are crosslinked to form a tissue matrix or from synthetic materials, such as polymers, that have or have had viable cells associated with the matrix. Thus, tissue materials have viable cells or structures formed from cells that are no longer present. Suitable polymers, such as polyesters, and extracellular matrix proteins, such as collagen, elastin and combinations thereof, for incorporation into a synthetic tissue matrix are commercially available. A tissue material can form the entire prosthetic conduit or it can form one or more portions of the prosthetic conduit.

Natural, i.e. biological, tissue material for use in the invention includes relatively intact tissue as well as decellularized tissue. These natural tissues may be obtained from, for example, native heart valves, portions of native heart valves such as roots, walls and leaflets, pericardial tissues such as pericardial patches, amniotic sacs, connective tissues, bypass grafts, tendons, ligaments, skin patches, blood vessels, cartilage, dura mater, skin, bone, fascia, submucosa, umbilical tissues, and the like. Natural tissues are derived from a particular animal species, typically mammalian, such as human, bovine, equine, ovine, porcine, seal or kangaroo. These tissues may include a whole organ, a portion of an organ or structural tissue components.

Suitable natural tissues include xenografts, homografts and autografts. These natural tissues generally include collagen-containing material. Natural tissue is typically, but not necessarily, soft tissue. Tissue materials are particularly useful for the formation of tissue heart valve prostheses. The tissue can be decellularized.

Tissue materials can be fixed by crosslinking. Fixation provides mechanical stabilization, for example, by preventing enzymatic degradation of the tissue. Glutaraldehyde, formaldehyde or a combination thereof is typically used for fixation, but other fixatives can be used, such as epoxides, epoxyamines, diimides and other difunctional aldehydes. In particular, aldehyde functional groups are highly reactive with amine groups in proteins, such as collagen. Formaldehyde generally does not function alone as a satisfactory crosslinking agent. However, formaldehyde is a common sterilant used to store tissue following glutaraldehyde crosslinking. Epoxyamines are molecules that generally include both an amine moiety (e.g. a primary, secondary, tertiary, or quaternary amine) and an epoxide moiety. The epoxyamine compound can be a monoepoxyamine compound and/or a polyepoxyamine compound. In some embodiments, the epoxyamine compound is a polyepoxyamine compound having at least two epoxide moieties and possibly three or more epoxide moieties. In some preferred embodiments, the polyepoxyamine compound is triglycidylamine (TGA).

Suitable synthetic materials for incorporation into a prosthetic conduit include polymers. Polymeric materials can be fabricated from synthetic polymers as well as purified biological polymers. Appropriate synthetic polymers include, for example, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethylsiloxanes, cellulose acetates, polymethyl methacrylates, ethylene vinyl acetates, polysulfones, nitrocelluloses and mixtures, derivative and copolymers thereof. These synthetic polymeric materials can be woven or knitted into a mesh to form a matrix or substrate. Alternatively, the synthetic polymer materials can be molded or cast into appropriate forms. Biological polymers can be naturally occurring or produced in vitro by fermentation and the like or by recombinant genetic engineering. Suitable biological polymers include, for example, collagen, elastin, silk, keratin, gelatin, polyamino acids, polysaccharides (e.g., cellulose and starch) and copolymers thereof. Polymer materials can be impregnated with structural proteins, such as collagen, to impart desired levels of resistance to leaking.

The reinforcements can be formed from natural materials, synthetic materials or a combination thereof. The reinforcement preferably is somewhat flexible, although the reinforcement generally is formed from a durable and non-extensible material. In general, the reinforcement can be formed from one or more layers of tissue, such as pericardium, that is placed around the prosthetic conduit and sutured, stapled, glued or otherwise fastened around the conduit. The reinforcement can be similarly formed from one or more layers of fabric or other polymer sheeting. Similarly, the reinforcement can be formed from a roll of tissue or synthetic material. Also, the reinforcement can be formed from bands of metal or other inorganic material.

Sewing rings can be formed also from tissue materials and/or synthetic polymer materials. In addition to the synthetic polymers described above, sewing rings can be formed from bioresorbable polymers. Suitable bioresorbable polymers include, for example, dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly (hydroxy butyrate), and similar copolymers.

Prosthetic Heart Valves

The aortic heart valve or the pulmonary heart valve can be replaced along with the portion of the aorta or pulmonary artery. The valve can be secured to native structure during implantation, or the prosthetic valve can be combined with a portion of the prosthetic conduit. Specifically, mechanical valves can be secured to the native valve root or to a prosthetic conduit. A valve with flexible leaflets can be secured to both the native valve root and a portion of the native artery extending from the native valve root or, alternatively, to a portion of the prosthetic conduit that is then fastened to the native valve root. If the valve is secured to native structure, the implantation of the prosthetic valve can be performed in the same surgical procedure as the replacement of an adjacent section of aorta or pulmonary artery with the prosthetic conduit.

A representative mechanical heart valve is shown in FIG. 6. A bileaflet mechanical heart valve prosthesis 200 includes an orifice ring 202, which retains two occluders 204, 206. Occluders 204, 206 rotate at pivots 212, 214 and two additional opposed pivots (not shown) symmetrically positioned on the inner luminal surface 216 of orifice ring 202. Inner luminal surface 216 of orifice ring 202 forms a flow path through the valve that can be opened or closed by the pivoting of occluders 204, 206. Blood flows through valve 200 in an effectively unidirectional way. A sewing ring 218 is placed around orifice ring 202 to facilitate attachment with the patient's tissue during implantation of the valve. Other mechanical valves, including, for example, valves with a single leaflet or more than two leaflets or a ball and cage design, can be used in place of the particular embodiment in FIG. 6 as replacement for the native aortic valve or pulmonary valve.

Figure 7:
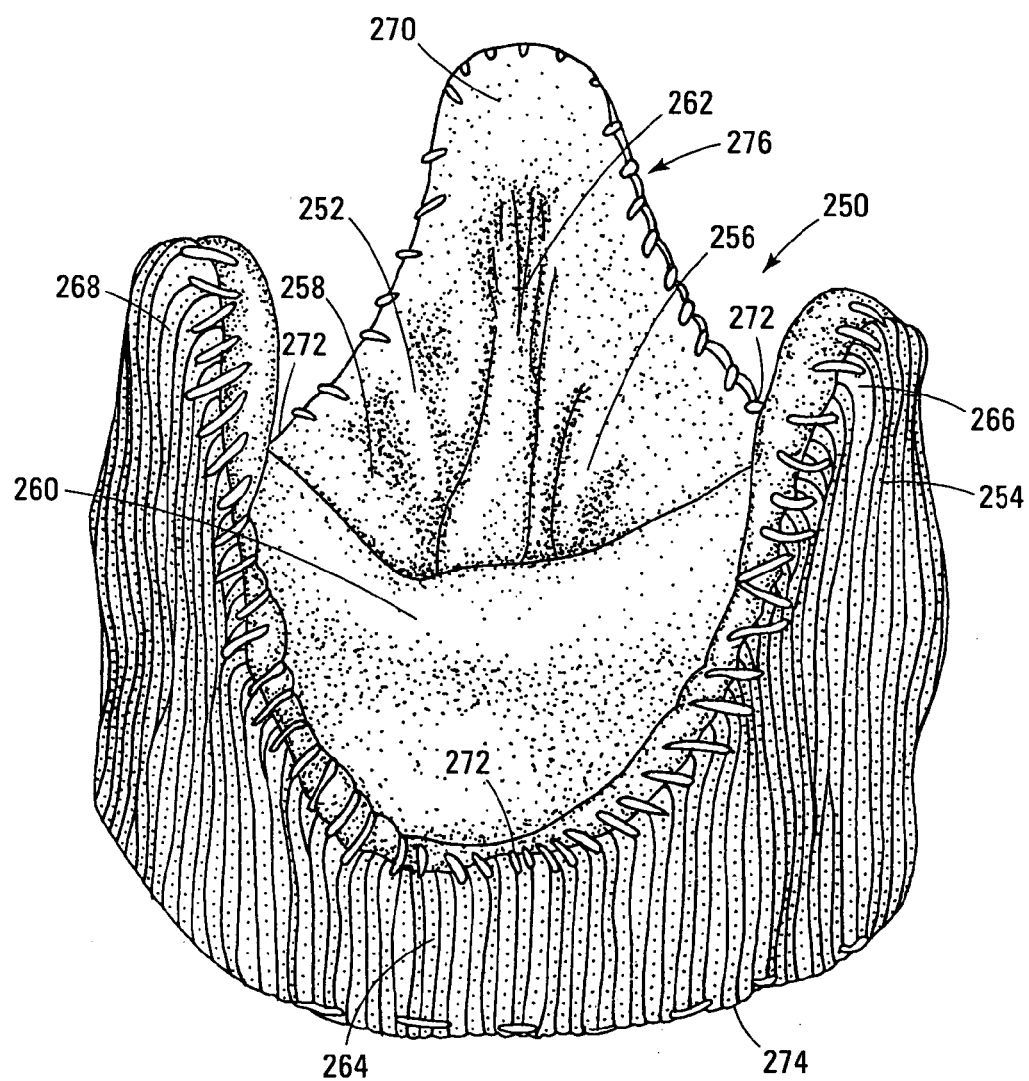
FIG. 7 is a perspective view of a stentless heart valve prosthesis.

An embodiment of a stentless tissue-based heart valve prosthesis is shown in FIG. 7. Heart valve prosthesis 250 includes a harvested tissue heart valve 252, such as a porcine valve. For implantation of a porcine valve into a human, harvested tissue valve 252 generally is crosslinked to reduce the immune response. Prosthesis 250 can further include a fabric cover 254. Valve 252 has three leaflets 256, 258, 260 that meet at coaptation surfaces 262. Valve 252 has a generally annular base 264 and three commissure supports 266, 268, 270 at which the free edge of the leaflets attach. Three scallops 272 extend between commissure supports 266, 268, 270 along the upper edge of the prosthesis. Lower edge 274 of prosthesis 250 is the inflow end, and upper edge 276 is the outflow end. In this embodiment, lower edge 274 is generally planar, in contrast with the scalloped upper edge 276 of the prosthesis. The prosthesis shown in FIG. 7 is suitable for implantation at the aortic or pulmonary positions in a heart.

Alternative embodiments of heart valve prostheses with flexible leaflets involve assembly of leaflets in a desired shape from a tissue or polymer material. One or more leaflets are assembled in association with a support structure to form either a stented or stentless valve, depending on the nature of the support structure. The support structure can be formed from natural materials, synthetic materials or a combination thereof.

A representative embodiment of a stented valve with flexible leaflets is shown in FIG. 8. Heart valve prosthesis 300 includes leaflets 302, 304, 306 and stent 308. Stent 308 includes commissure supports 310, 312, 314 and scallops 316, 318, 320 between the commissure supports. Free edges 322, 324, 326 of leaflets 302, 304, 306, respectively, join stent 308 at the commissure supports 310, 312, 314. Attached edges 328, 330, 332 of leaflets 302, 304, 306 also attach to stent 308 along scallops 316, 318, 320. Base 334 of stent/support structure 308 generally is a cylindrical ring that forms the opening into the valve at the upstream or inflow end of the valve. Other stented and stentless polymer and tissue based valves can similarly be used and may have fewer or more leaflets than the three leaflet valve shown in FIG. 8. The design of polymer leaflets for prosthetic heart valves is described further in copending and commonly assigned U.S. patent application Ser. No. 09/955,703 to Cai et al., entitled "POLYMER LEAFLET DESIGNS FOR MEDICAL DEVICES," incorporated herein by reference.

Prostheses With Conduits and Valves

The prostheses can include both a prosthetic conduit and a prosthetic valve. These prostheses can be a single integral unit with the valve integrated into a section of prosthetic conduit. Alternatively, the prostheses can include two or more sections of prosthetic conduit that fit together to form an entire conduit section with one section including the prosthetic valve. Whether or not a prosthesis has one or more sections of prosthetic conduit, a conduit for aortic replacement generally includes appropriate structure for the connection of the coronary arteries. Also, if the valve has a profile extending sufficiently into the artery, the valve should be mounted such that the valve commissure supports do not interfere with flow into the coronary arteries.

Figure 9:
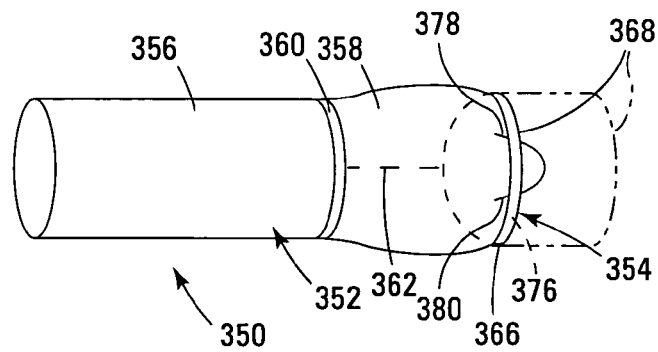
FIG. 9 is a cut-away perspective view of a prosthetic conduit with a portion of the conduit removed to expose a prosthetic valve.

A first embodiment of a prosthesis with a single prosthetic conduit portion and a prosthetic heart valve is shown in a cut-away view in FIG. 9. Prosthesis 350 includes prosthetic conduit 352 and mechanical heart valve 354. Prosthetic conduit 352 includes a generally cylindrical section 356, an expanded section 358 and optional reinforcement 360. This embodiment can be used for replacement of the pulmonary heart valve and a corresponding section of the pulmonary artery if the valve is placed is placed away from the inflow edge 368, as shown in phantom lines in FIG. 9. Also, the aortic valve and corresponding section of the aorta can be replaced with prosthesis 350 if the valve has a sufficiently low profile such that the coronary arteries can be connected to holes in the side of the conduit without interference from the valve leaflets. If it is desirable to orient the valve, markings 362 can be placed on the exterior of the prosthesis to correspond to the commissures of the valve. In alternative embodiments for the aorta, tubules can provide fluid communication between the interior of expanded section 358 and the exterior of conduit 352 for the attachment of coronary arteries.

Mechanical valve 354 and an optional sewing ring 366 are connected together with conduit 352 at the inflow edge 368 of conduit 352. In the embodiment of FIG. 9, mechanical valve 354 includes an orifice ring 376 and two leaflets 378, 380 that pivot to open and close the lumen within orifice ring 376. If prosthetic valve 354 has a profile that does not approach the locations for connecting the coronary arteries, the coronary arteries can be attached to the prosthesis without particular attention to the orientation of the valve.

The dimensions of prosthetic conduit 352 are generally similar to the dimensions of the prosthetic conduits in FIGS. 1–3 except that the expanded section covers the valve. In valved embodiments, the expanded 358 section generally reaches a maximum diameter along the axial, i.e., flow, direction and has a smaller diameter relative to the maximum at both the connection with the valve and the connection with the generally cylindrical section 356. The maximum diameter is generally equivalent to the maximum diameters for the embodiments in FIGS. 1–3. The diameter at the inflow edge is generally no more than about 10% greater than the average diameter of the generally cylindrical section and may be approximately equal to the average diameter of the generally cylindrical section. Suitable materials for formation of the prosthetic conduit are described above.

Figure 10:
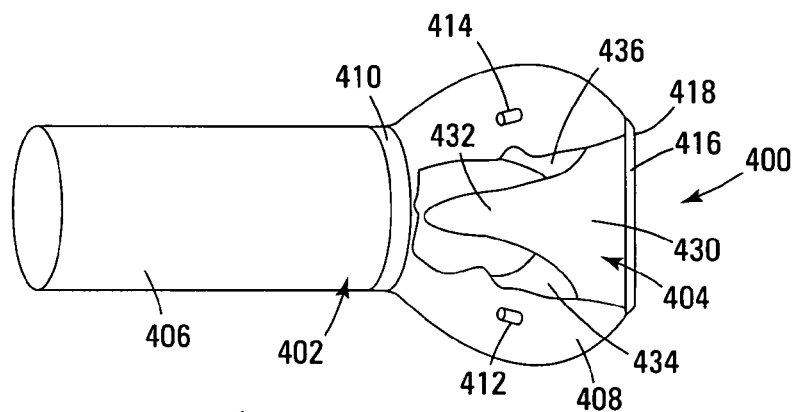
FIG. 10 is a cut-away perspective view of a prosthetic conduit with tubules for attachment of coronary arteries, with a portion of the conduit removed to expose a prosthetic valve.

An alternative embodiment of a valved prosthesis is shown in a cut-away view in FIG. 10. Prosthesis 400 includes a prosthetic conduit 402 and a prosthetic valve 404 having flexible leaflets. Prosthetic conduit 402 includes a generally cylindrical section 406, an expanded section 408 and a reinforcement 410. Optional tubules 412, 414 provide fluid communication between the interior of conduit 402 and the exterior of conduit 402 for the attachment of coronary arteries. Prosthetic valve 404 and optional sewing ring 416 and/or reinforcement are connected together with conduit 402 at the inflow edge 418 of conduit 402. In the embodiment of FIG. 10, prosthetic valve 404 includes a support structure 430 with commissure supports 432 (with one shown in FIG. 10) and flexible leaflets 434, 436. Prosthetic valve 404 can be stented or stentless. The inflow edge generally can be planar or scalloped. Prosthetic valve 404 can include one, two, three or more flexible leaflets and a corresponding number of commissure supports to support the leaflets.

Commissure supports 432 are oriented such that the commissure supports do not block the flow into tubules 412, 414. Thus, by taking into account the orientation of valve 404 relative to the tubules during the manufacture of prosthesis 400, the surgeon does not need to worry about the orientation of valve 404 during implantation other than orienting the tubules for attachment of the coronary arteries. By attaching the coronary arteries at tubules 412, 414, proper function of the prosthesis is obtained without any inappropriate blockage due to the valve commissures. Valve 404 can be stented or stentless. If valve 404 is stentless, support structure 430 is attached to the inner walls of expanded section 408 to maintain valve function against fluid pressures. For embodiments with stentless valves, the support structure generally cannot be expanded significantly without effecting proper coaptation of the leaflets, although the support structure may flare out slightly. Thus, the expanded section forms lobes between the commissures and scallops of the support structure. While the inflow edge is shown as planar, the inflow edge can include a slight scalloped shape to facilitate attachment to the native annulus following removal of the native leaflets.

Embodiments similar to the prosthesis in FIG. 10 without tubules can be used for replacement of the pulmonary heart valve and adjacent section of the pulmonary artery. Similarly, the aortic heart valve and adjacent section of aorta can be replaced with an embodiment similar to the prosthesis in FIG. 10 without tubules 412, 414 if attachment of the coronary arteries can be performed without interference from the commissure supports. In particular, embodiments without tubules can be used for aortic implantation if appropriate markings are placed on the outside of the prosthesis to direct the surgeon how to orient the valve and/or to indicate appropriate locations for the attachment of the coronary arteries. For example, the outline of the commissure supports can be marked on the outside of section 408 such that holes can be made away from the commissure supports for attachment of the coronary arteries. The markings of the commissure supports can be similarly used to orient the prosthesis for implantation. In additional embodiments, expanded section 408 and/or reinforcement 410 can be omitted. For example, tubules 412, 414 can be attached directly to generally cylindrical section 406 that connects to the prosthetic valve. While such embodiments would not have the advantages provided by the expanded section, the presence of the tubules can provide advantages for the attachment of the coronary arteries. Similar variations are possible for the embodiment shown in FIG. 9.

Additional embodiments of the prosthesis include two or more sections of conduit that are connected to complete the prosthesis. While these sections can be implanted in any order, generally the valved section is implanted first, then the non-valved section(s) is (are) attached to the valved section, and the artery is attached to the implanted prosthesis. A first embodiment of a prosthesis with multiple sections of prosthetic conduit is shown in a cut-away view in FIG. 11. Prosthesis 450 includes a first section 452 and second section 454. First section 452 includes a generally cylindrical portion 456, a reinforcement 458, an expanded attachment section 460 and an optional sewing ring 462. Expanded attachment section 460 attaches to second section 454. The size of expanded attachment section 460 can be selected to facilitate connection of first section 452 and second section 454 as long as expanded attachment section 460 does not interfere with attachment of the coronary arteries.

Figure 11:
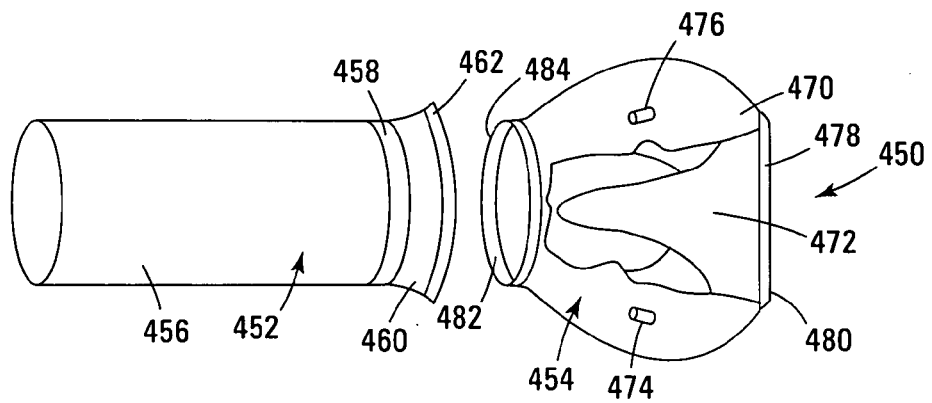
FIG. 11 is a cut-away perspective view of a two-piece prosthetic conduit, with a portion of the expanded section of the conduit removed to expose a prosthetic valve.

Second section 454 includes an expanded prosthetic conduit 470 and a prosthetic valve 472. Expanded prosthetic conduit 470 generally has curved walls and has a larger average diameter than generally cylindrical portion 456. Expanded prosthetic conduit 470 corresponds with the expanded sections of the prostheses in FIGS. 1–3, 9 and 10. As shown in FIG. 11, prosthetic valve 472 has flexible leaflets, although a mechanical valve can be substituted for the valve with flexible leaflets. Second section 454 further includes tubules 474, 476 for connection of the coronary arteries. Since the orientation of the valve is sufficiently visible when first section 452 is not attached, the prosthetic conduit is designed without tubules in alternative embodiments while still providing for the attachment of the coronary arteries. Thus, the second section 454 can be oriented visibly by the surgeon during implantation to allow for attachment of the coronary arteries at a hole in the prosthesis without resulting in blockage of flow into the arteries by the valve structure. Second section 454 also has an optional sewing ring 478 and/or reinforcement at the inflow edge 480 and an optional sewing ring 482 and/or reinforcement at the outflow edge 484.

Figure 12:
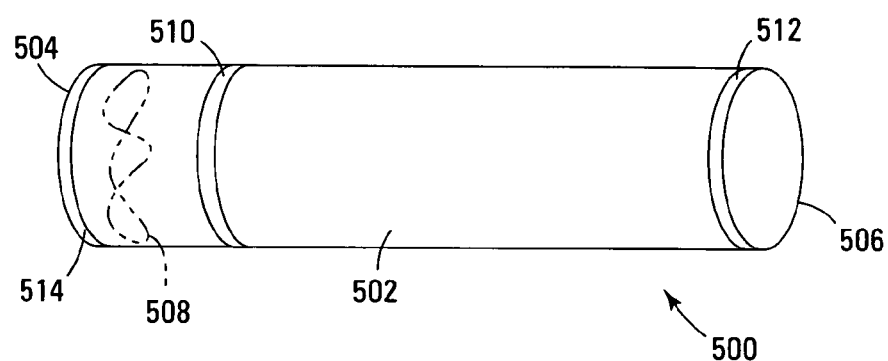
FIG. 12 is a perspective view of a prosthetic conduit having a reinforcement near a prosthetic valve to resist dilation of the conduit downstream from the valve, with the valve shown schematically in phantom lines.

Some improved embodiments for replacement of the aorta can include reinforcements even without an expanded section. Referring to FIG. 12, prosthesis 500 includes a generally cylindrical prosthetic conduit 502 having an inflow edge 504 and an outflow edge 506, a valve 508, shown schematically in phantom lines within prosthetic conduit 502. Prosthetic conduit 502 can have one or more reinforcements. As shown in FIG. 12, prosthetic conduit 502 comprises a reinforcement 510 near the outflow edge of valve 508, reinforcement 512 near the outflow edge and reinforcement 514 near the inflow edge. Reinforcements 510, 512 and 514 reduce or eliminate dilation of the conduit due to fluid pressures.

Figure 13:
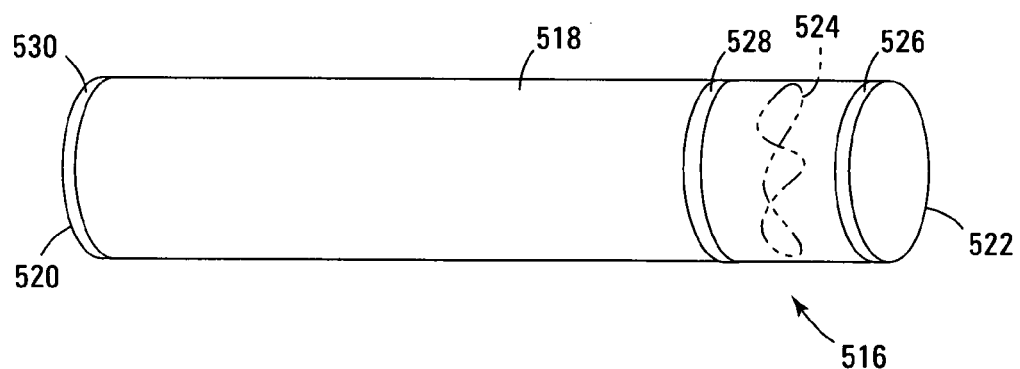
FIG. 13 is a perspective view of a prosthetic conduit having a reinforcement near the outflow edge, with a prosthetic valve shown schematically in phantom lines.

In embodiments for the replacement of the pulmonary artery, it may be particularly desirable to have a reinforcement at or near the outflow edge to prevent collapse of the prosthetic conduit due to pressure drops. Pressure at the outflow edge can reach values, for example, that are ⅕ of the pressure at the inflow edge. Referring to FIG. 13, prosthesis 516 has a prosthetic conduit 518 having an inflow edge 520 and an outflow edge 522, an optional valve 524, shown schematically in phantom lines within prosthetic conduit 518. In relevant embodiments, inflow edge 520 is generally about one centimeter to about 5 centimeters from valve 524. Prosthetic conduit 518 can have one or more reinforcements. As shown in FIG. 13, prosthetic conduit includes an outflow edge reinforcement 526, a reinforcement 528 near the inflow edge of valve 524 and reinforcement 530 near inflow edge 520. Generally, outflow edge reinforcement 526 is placed at the edge or within about one centimeter of the outflow of the valve. Outflow edge reinforcement 526 is generally stiff and is attached to prosthetic conduit 518 to resist collapse of the conduit. Outflow reinforcement 526 can have similar dimensions and can be formed from similar materials as other reinforcements. Reinforcement 530 may be oblong or oval shape and is generally stiff, although the reinforcement can be bendable to allow for adjustment in anatomy. Correspondingly, inflow edge 520 can be at an angle relative to the central axis of prosthetic conduit 518 to facilitate attachment to the heart.

Construction of the Prosthetic Conduits

The various embodiments of the prostheses can be assembled from appropriate sections of material. Using either natural or synthetic materials, prosthetic conduits can be formed directly from conduit shaped components. However, in other embodiments, prosthetic conduits are formed at least partially from sheet material with appropriate processing to form the curved portions of the prosthetic conduit. While the details of the assembly process will depend on the specific features of the prosthesis, these details can be adapted from the general description that follows.

With respect to tissue materials, a xenograft aorta with the natural sinuses or pulmonary artery with the natural sinuses can be used for the prosthetic conduit following fixing, trimming, cutting to the desired dimensions, and other treatment. The natural conduits can be opened up for the attachment of a prosthetic valve, if desired, and reassembled to reestablish the conduit form using suture, staples, biocompatible adhesive, other like fasteners or combinations thereof. Suitable biocompatible adhesives are commercially available, for example, as surgical adhesives. Other natural conduits, such as intestine, bronchus or other large artery or vein, also can be adapted for use in the present prostheses. With respect to synthetic materials, polymers and the like can be extruded, molded, woven or cast into a shape, including the curves of the sinuses. As with natural tissue conduits, the formed synthetic materials can be opened up for the attachment of a prosthetic valve and reassembled to form the conduit. However, in other embodiments, a wide range of materials can be used if the materials are conformed into the desired shape, generally from planar sheet material.

Figure 14:
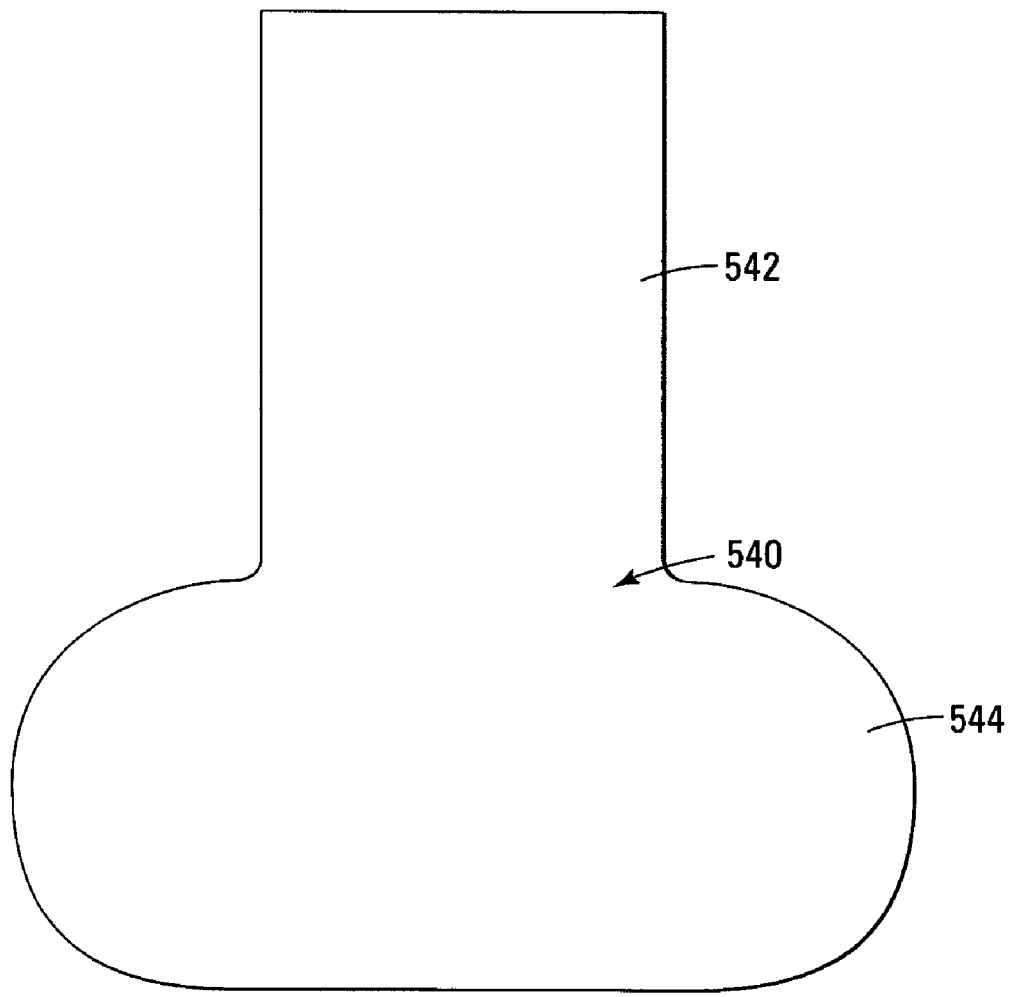
FIG. 14 is a top view of a cut sheet of material for formation into a prosthetic conduit with an expanded section at a location corresponding to sinuses of Valsalva.

For a tissue-based prosthetic conduit without a valve, several illustrative approaches can be used for forming the prosthesis from initially planar, i.e., sheet, material. For example, the prosthetic conduit can be formed from a sheet of material, either tissue, such as pericardium, polymer, such as fabric, or other appropriate biocompatible material, that is shaped to accommodate the different diameters at the different portions of the prosthetic conduit. A representative sheet of material cut in a suitable form is shown in FIG. 14. Specifically, sheet 540 has a rectangular portion 542 and an expanded section 544. Rectangular portion 542 can be folded around a cylindrical shaft to bring the opposite edges together. The opposite edges can be stitched, glued or otherwised fastened to form a generally cylindrical section of the resulting prosthetic conduit. In addition, the opposite edges of the expanded section 544 can be fastened together to form the extended section of the resulting prosthetic conduit. While the resulting structure formed from connecting the attached edges of expanded section 544 may not have a balloon shape, it would have roughly the variation in diameter desired. Also, it can be placed over a spherical or other comparable shape to help the material conform more closely to a desired shape. A person of ordinary skill in the art will recognize that various shapes can function appropriately depending on the overall structure of the prosthetic conduit.

Figure 15:
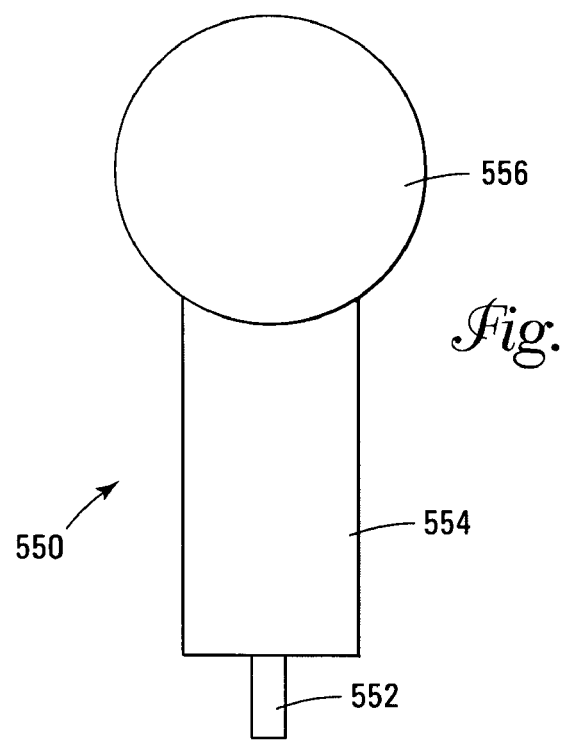
FIG. 15 is a side view of a mandrel for the formation of a sheet of material into a prosthetic conduit with an expanded section at a location which would correspond to sinuses of Valsalva.

Similarly, a rectangular or curved shape of planar tissue or other material can be placed over a mandrel having a desired shape to conform the material to the shape due to tension on the material against the mandrel. Tissue and some polymers will gradually distort to the shape of the mandrel if it is secured to the mandrel with the application of tension. An appropriate mandrel is shown in FIG. 15. Mandrel 550 includes a handle 552, a generally cylindrical section 554 and a curved section 556. Handle 552 provides for holding, supporting and moving the mandrel and can have convenient shape and size consistent with its function. For two component prostheses, generally two mandrels, one for each component, is used to shape the components.

Generally cylindrical section 554 provides for the formation of a generally cylindrical section of the prosthetic conduit, and curved section 556 provides for the formation of the expanded section of the prosthetic conduit. Generally cylindrical section 554 and curved section 556 have appropriate sizes and shapes to form the corresponding sections. The top of curved section 556 generally can have any convenient shape since the material typically does not extend over the top of curved section 556. The tissue or other material is fastened temporarily to mandrel 550 since the material must be removed from the mandrel for use. For example, suction, a non-permanent biocompatible adhesive or suture can be used for the temporary mounting onto the mandrel. After removing the contoured material from the mandrel, a permanent seam can be put in place with suture, permanent adhesive or other fastener.

Figure 16:
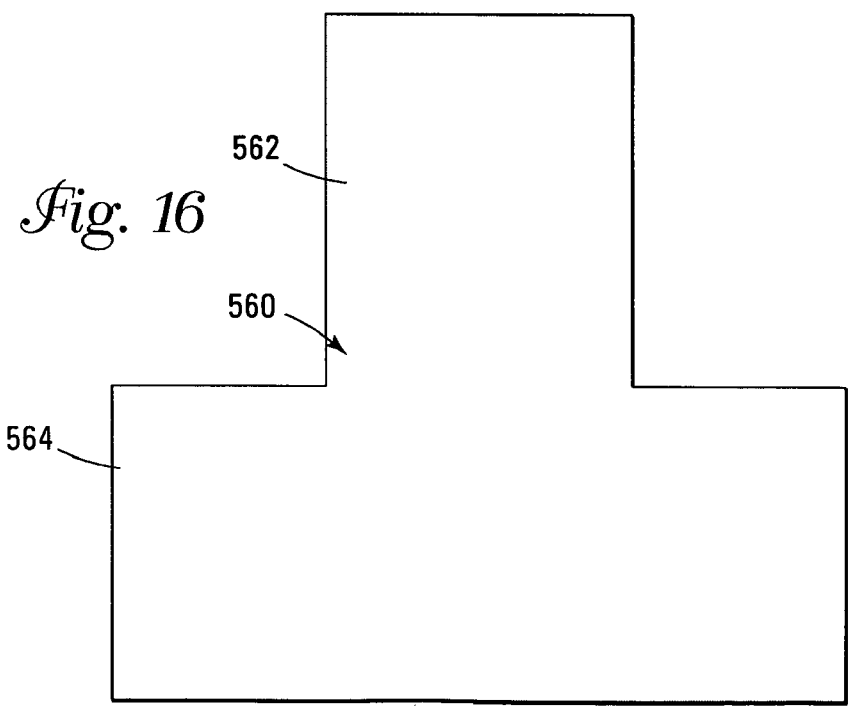
FIG. 16 is a top view of a sheet of material cut with straight edges for formation into a prosthetic conduit with an expanded section at a location which would correspond to sinuses of Valsalva.

With the use of a mandrel, the initial shape of the tissue or other material is somewhat less important since, to achieve the desired shape, the material can distort to conform to the mandrel. Overlap of material in the contoured configuration generally would not detract from the properties of the prosthesis. Thus, a material section with rectangular sections can be used, as shown in FIG. 16. Material section 560 has a first rectangular section 562, for forming the generally cylindrical section of the conduit, and a second rectangular section 564, for forming the expanded section of the conduit. Second rectangular section 564 is conformed to the shape of a mandrel to introduce desired curvature. More elaborate planar cuts can be performed. For example, the three dimensional shape that is desired can be formed as a planar projection that assembles directly into the approximate three dimensional shape. These cut sections can involve cut out sections such that the folds more closely assemble into the desired three dimensional surface similar to planar map projections of a globe. The object can be folded into the correct shape or placed on a mandrel with the seams sutured, glued or otherwise fastened to form the desired shape.

The cutting of the tissue or other material to the appropriate shape can be performed by hand by a skilled technician. The material can be cut along a die or with a die with sharp edges. Alternatively, focused beam cutting can be used to introduce more automated features to the process. Focused beam cutting of tissue and other materials for the formation of prostheses is described, for example, in copending and commonly assigned U.S. patent application Ser. No. 09/755,424 to Guzik, entitled "Focused Beam Cutting Of Materials," incorporated herein by reference.

Figure 17:
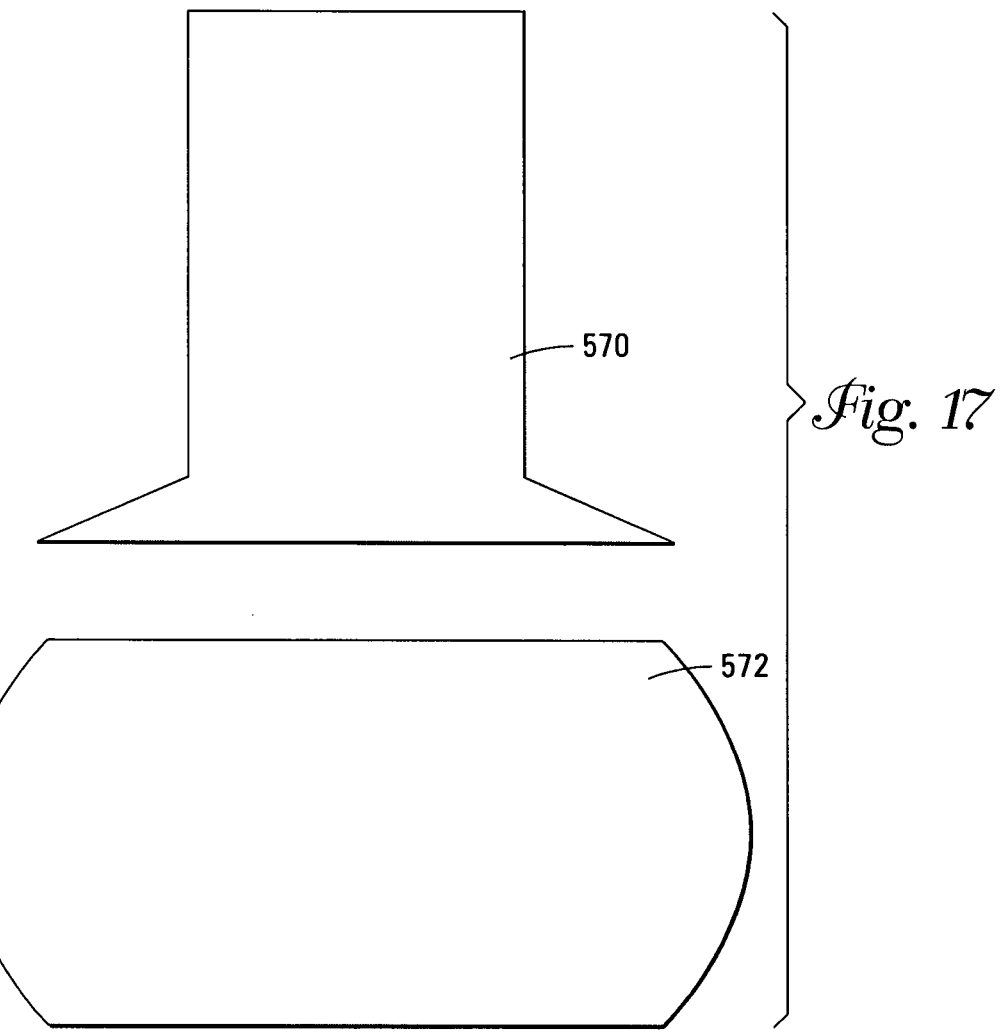
FIG. 17 is a top view of two sheets of material for formation into a two section prosthetic conduit having an expanded section.

To form the two-piece prosthetic conduit embodiments, such as the embodiment in FIG. 11, corresponding portions of material can be used to form each piece. For example, referring to FIG. 17, segments 570, 572 can be configured to form two elements of a prosthetic conduit that fit together to form a complete prosthetic conduit. Element 570 can be wrapped around a cylindrical member to form a generally cylindrical prosthetic conduit element with a portion for connecting to an expanded section. Element 572 can be wrapped to form an expanded section of a prosthetic conduit. In some embodiments, the expanded section becomes a valved portion of the prosthetic conduit. Element 572 can be wrapped around a spherical mandrel or other convenient shape that provides for joining the opposite edges to form a reasonably shaped expanded section. A one-piece prosthesis can be formed in two or more pieces that are connected to form the prosthesis. In these embodiments, each piece can be separately shaped.

A prosthetic heart valve can be fastened to the appropriate prosthetic conduit before, during or after formation of the prosthetic conduit into the appropriate shape. In particular, mechanical valves, due to their relatively low profile, can be fastened to the prosthetic conduit after forming the conduit. The mechanical valve can be connected at the inflow edge of the prosthetic conduit with an attachment around the base of the valve, such as a single suture line, an adhesive bond, staples or the like. A stented prosthetic valve with flexible leaflets can be attached similarly to a mechanical valve since only the inflow edge is attached. The stent maintains leaflet function against fluid pressures without any further attachment of the commissure supports.

A stentless prosthetic valve with flexible leaflets generally requires attachment of the commissure supports to the prosthetic conduit. Thus, a stentless prosthetic valve with flexible leaflets requires fastening at the inflow edge and the outflow edge. The outflow edge can be somewhat difficult to fasten within a prosthetic conduit, such as the conduits in FIGS. 1–3. Alternatively, the inflow edge can be fastened within an expanded prosthetic conduit component, such as second section 454 of FIG. 11. The outflow edge of the expanded section of the two component conduit prosthesis provides some access to the outflow edge of the valve within the conduit.

Figure 18:
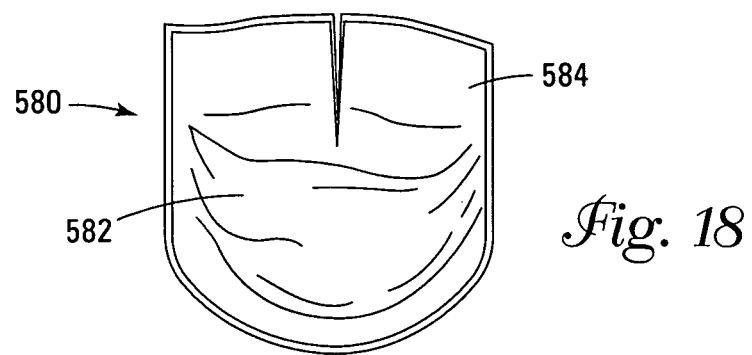
FIG. 18 is a top view of a leaflet for formation into a prosthetic valve.
Figure 19:
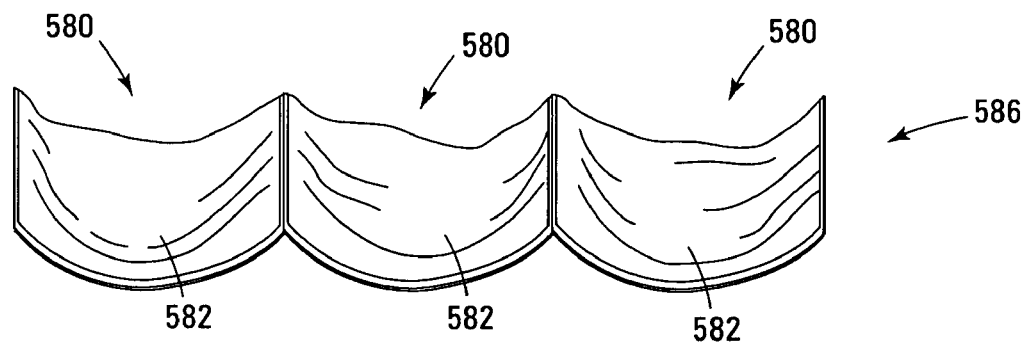
FIG. 19 is a top view of three leaflets of FIG. 18 joined together.
Figure 20:
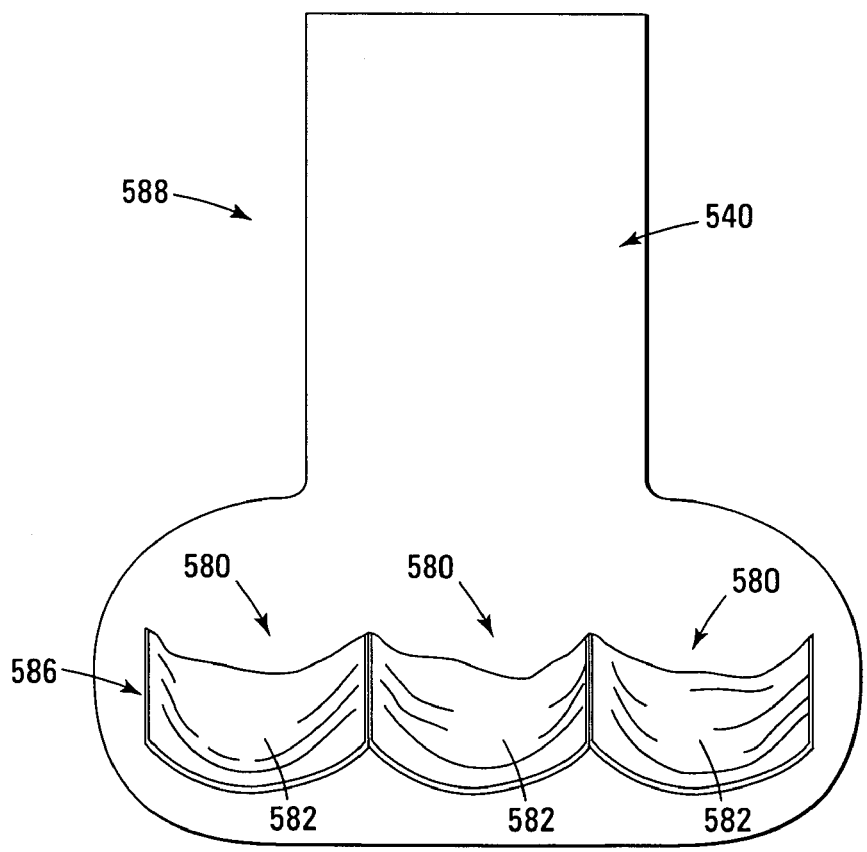
FIG. 20 is a top view of three leaflets joined to a section of material to form a structure that can be contoured to form a prosthetic conduit with a prosthetic valve having flexible leaflets in which the prosthetic conduit has an expanded section.

In other embodiments, the inflow edge of the valve can be fastened to the conduit material as the prosthetic conduit portion is curved into the desired shape such that the contouring of the conduit and the fastening of the inflow edge, and possibly outflow edge, is performed as part of the operation of forming the conduit. The conduit material can cover the valve to introduce some shape along the inflow edge of the conduit, such as a slight scallop shape, to facilitate implantation along the natural annulus. In still other embodiments, individual leaflets can be fastened to the material forming the prosthetic conduit before the material is shaped and fastened into the conduit configuration. For example, a leaflet section 580 includes an individual leaflet 582 along with a portion of the aortic wall 584, as a support structure, as shown in FIG. 18. Leaflet sections 580, for example, can be harvested from a porcine valve or formed from pericardium. The leaflet component can be cut from a sheet of pericardium and shaped to have the scallop shape of the attached edge and the proper dimensions of the free edge to have desired coaptation when assembled with the other leaflets. Three leaflet sections 580 can be attached individually to the prosthetic conduit material, or the leaflets can first be fastened together to form a three leaflet section 586, as shown in FIG. 19. Referring to FIG. 20, three leaflet section 586 is attached to sheet 540 to form a valved-conduit form 588 that is contoured into a valved-conduit prosthesis.

Figure 21:
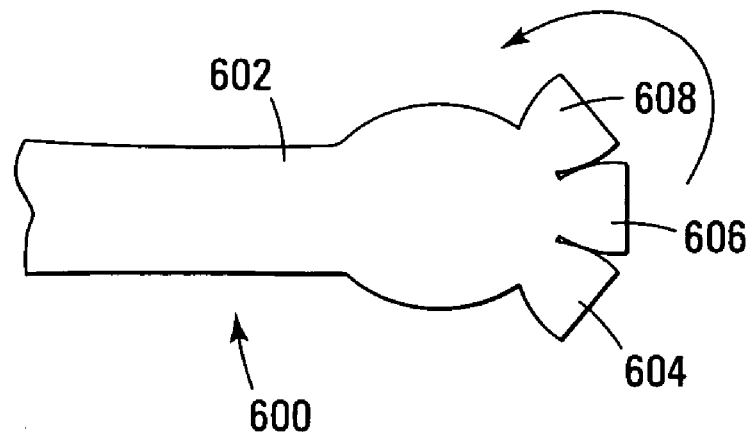
FIG. 21 is a top view of a sheet of tissue cut to include leaflets sections that can be folded into position along the prosthetic conduit.
Figure 22:
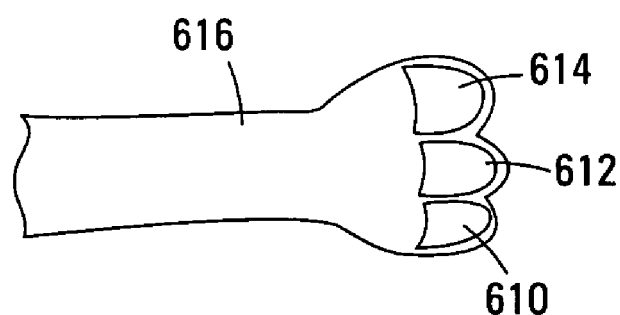
FIG. 22 is a top view of a sheet of sheet of tissue for a prosthetic conduit with cut leaflet sections attached.

In addition, the conduit and the leaflets can be cut from sheets of biocompatible material, such as pericardium. In one embodiment, the leaflets are cut as a part of the conduit and the leaflet portions are folded into place and fastened. Referring to FIG. 21, cut tissue portion 600 includes a prosthetic conduit section 602 and three leaflet sections 604, 606, 608. Leaflet sections 604, 606, 608 are folded, as shown with the arrow, and fastened to position the leaflets along the prosthetic conduit. The conduit section is then contoured and fastened to form the prosthetic conduit with the leaflets appropriately positioned for valve function. Similarly, the leaflet sections can be cut from the same or a separate sheet of pericardium, or other biocompatible material, and fastened to the appropriate location on the section of biocompatible material to be formed into the prosthetic conduit. Referring to FIG. 22, leaflet sections 610, 612, 614 are fastened to prosthetic conduit section 616. The conduit section is contoured and fastened to form the prosthetic conduit.

Implantation of the Prostheses

The procedure for implanting the prosthetic conduit varies depending on the particular embodiment of the prosthesis and whether or not the corresponding heart valve is also replaced. Generally, with any of the prostheses, the patient is placed on cardiopulmonary bypass, and the patient's chest cavity is opened to provide access to the appropriate artery at the connection with the heart. An appropriate section of the artery is removed for replacement/reconstruction.

If the heart valve is not replaced, the artery is cut near the heart along the sinuses of Valsalva with care not to damage the leaflets of the heart valve. The artery is also cut downstream from the sinuses such that the portion of the artery can be removed and replaced. Generally, the artery can be cut along the commissures and scallops of the valve. While the artery is severed, the heart valve can be accessed for examination and/or any repair. The removed section of artery can be replaced with an embodiment of the improved prosthetic conduits described herein. In particular, for appropriate embodiments, an expanded section of the prosthetic conduit is attached along the cut sinuses. The generally cylindrical section of the prosthetic conduit is attached to the other free end of the artery. Suture or alternatives to suture, such as staples, barbed pins, surgical adhesives and the like, can be used to secure the prosthetic conduit to remaining portions of the native artery.

For the aorta, the coronary arteries may or may not be disconnected when the aorta is cut along the sinuses. Generally, the coronary arteries are cut along the surface of the aorta and reattached to the expanded section of the prosthetic conduit. For example, the coronary arteries can be inserted into a hole in the prosthetic conduit and sutured in place, or can be attached to a tubule and sutured in place. Again, suture or alternatives to suture can be used to secure the coronary arteries to the prosthetic conduit. The presence of the expanded section of the prosthetic conduit facilitates the reattachment of the coronary arteries since the expanded section of the prosthetic conduit is similar to the native structure such that significant repositioning of the coronary arteries should not be necessary to reach the prosthesis for attachment.

As noted above, the heart valve is accessible when the portion of the aorta or pulmonary artery is removed for reconstruction. While the valve is accessible, the valve can be replaced without replacing the corresponding section of the artery adjacent the heart. In particular, with the valve accessible through the open end of the artery, the leaflets of the native valve can be removed with a scissors or the like. With the valve removed, a mechanical heart valve can be attached at the native valve root. Similarly, a stented or stentless valve with tissue or polymer flexible leaflets can be implanted. A stented valve can be implanted by attachment at the native root similar to a mechanical prosthetic heart valve. A stentless valve with flexible leaflets is generally attached at both edges of the valve. The inflow edge is secured at the native root while the outflow edge of the valve is secured to the artery wall through the opening of the artery.

Alternatively, the heart valve can be replaced along with the corresponding section of artery. A one piece or a multiple-piece prosthetic conduit can be used with the heart valve attached to an appropriate portion of the prosthetic conduit. Since the prosthetic valve is attached to the prosthetic conduit, the heart valve is not separately implanted with these embodiments. Thus, the implantation of the prosthetic conduit also results in the replacement of the heart valve. The prosthesis can be fastened to the heart with suture, staples, barbed pins, surgical adhesives and the like. In contrast with some of the other embodiments, the native artery is detached at the location of the valve. With this approach, the sinuses of the native structure are removed and replaced with the prosthetic conduit. For the aorta, the coronary arteries can be reattached at a hole in the prosthetic conduit, or can be attached at a tubule extending from the prosthetic conduit. As with the other embodiments, the presence of an expanded section facilitates attachment of the coronary arteries. Facilitating the replacement of the heart valve and/or reattachment of the coronary arteries can shorten the surgical time and correspondingly reduce the time during which the patient is subjected to cardiopulmonary bypass. Decreasing the amount of time on a cardiopulmonary bypass can reduce risk to the patient.

Storing and Distribution

The prosthetic conduits with or without prosthetic valves can be stored following their formation. The appropriate storage technique depends on the nature of the materials incorporated in the prosthesis. Preferred storage techniques minimize the risk of microbial contamination. Prostheses with tissue components can be stored under conditions that keep the tissue from drying out. For example, prostheses with tissue components can be stored in a sealed container with sterile buffer, saline solution and/or an antimicrobial agent, such as formaldehyde, glutaraldehyde or alcohol. Prostheses without any tissue components generally can be stored in dry, sealed containers. The containers can be sterilized prior to sealing, for example, with steam, ethylene oxide, beta propriolactone, chlorine dioxide, gamma radiation, ozone or combinations thereof, or following sealing, using, for example, heat, steam, ethylene oxide or radiation, such as microwaves, gamma radiation or electron beam radiation.

The prostheses generally are packaged in sealed and sterile containers for shipping. To ensure maintenance of acceptable levels of sterility, prostheses, including tissue, can be transferred to the sterile container using accepted aseptic protocols. The containers can be dated such that the date reflects the maximum advisable storage time.

The containers generally are packaged with instructions for the use of the medical devices along with desired and/or required labels. The containers with the prosthetic conduits are distributed to health care professionals for use in appropriate medical procedures, such as implantation of the prosthesis and the like. The implantation is performed by a qualified health care professional.

The embodiments described above are intended to be illustrative and not limiting. Additional embodiments are within the claims below. Although the present invention has been described with reference to particular embodiments, workers skilled in the art will recognize that changes may be made in form and detail without departing from the spirit and scope of the invention.

What we claim is:

1. A prosthesis comprising:
   a reinforcement element and
   a prosthetic conduit comprising biocompatible material, the prosthetic conduit having a generally cylindrical section having a generally straight surface in an axial direction and an expanded section extending from an end of the generally cylindrical section to an edge shaped for attachment around a heart valve,
   wherein the reinforcement element is circumferentially positioned at the junction between the generally cylindrical section and the expanded section.

2. The prosthesis of claim 1 wherein the biocompatible material comprises tissue.

3. The prosthesis of claim 2 wherein the tissue comprises pericardium, submucosa or dura mater.

4. The prosthesis of claim 2 wherein the tissue comprises porcine, ovine, equine or bovine tissue.

5. The prosthesis of claim 2 wherein the tissue comprises crosslinked tissue.

6. The prosthesis of claim 5 wherein the tissue is crosslinked with glutaraldehyde or triglycidylamine.

7. The prosthesis of claim 1 wherein the biocompatible material comprises at least two segments joined to form the conduit.

8. The prosthesis of claim 7 wherein one segment forms the generally cylindrical section and a portion of the expanded section.

9. The prosthesis of claim 1 wherein the biocompatible material comprises a single segment.

10. The prosthesis of claim 1 wherein the expanded section has a maximum diameter at least about 10% larger than the average diameter of the generally cylindrical section.

11. The prosthesis of claim 1 wherein the expanded section has a maximum diameter from about 12% to about 20% larger than the average diameter of the generally cylindrical section.

12. The prosthesis of claim 1 wherein the expanded section has scallops along its free edge for attachment around a native aortic heart valve.

13. The prosthesis of claim 1 further comprising a prosthetic valve connected to the expanded section.

14. The prosthesis of claim 13 wherein the prosthetic valve comprises a rigid leaflet connected to an orifice ring.

15. The prosthesis of claim 13 wherein the prosthetic valve comprises tissue leaflets.

16. The prosthesis of claim 13 wherein the prosthetic valve comprises flexible polymer leaflets.

17. The prosthesis of claim 1 wherein the expanded section comprises tubules positioned for the attachment of the right and left coronary arteries.

18. The prosthesis of claim 1 wherein the expanded section has two components that connect together to complete the formation of the expanded section.

19. The prosthesis of claim 1 wherein the reinforcement element is a ring.

20. The prosthesis of claim 1 wherein the reinforcement element comprises tissue.

21. The prosthesis of claim 1 wherein the reinforcement element comprises a polymer.

22. The prosthesis of claim 21 wherein the polymer is woven into a fabric.

23. The prosthesis of claim 1 wherein the reinforcement element comprises metal.

24. The prosthesis of claim 1 wherein the reinforcement element is a band of pericardium.

25. The prosthesis of claim 1 wherein the reinforcement element is a roll of tissue.

26. The prosthesis of claim 1 wherein the reinforcement element surrounds the circumference of the biocompatible material.

27. The prosthesis of claim 1 wherein the reinforcement element surrounds only a portion of the circumference of the biocompatible material.

28. The prosthesis of claim 1 wherein the prosthetic conduit has a reinforcement near the inflow edge.

29. The prosthesis of claim 1 wherein the prosthetic conduit has a reinforcement near the outflow edge.

30. A prosthesis comprising:
    a biocompatible material formed into a generally cylindrical section that has a generally straight surface in an axial direction and
    an expanded section extending from the generally cylindrical section, the expanded section including tubules connecting the central lumen of the expanded section to an external opening.

31. The prosthesis of claim 30 wherein the tubules are positioned for the attachment of the right and left coronary arteries.

32. The prosthesis of claim 30 wherein the biocompatible material comprises at least two sections of material that join together to form the generally cylindrical section and the expanded section.

33. The prosthesis of claim 30 further comprising a prosthetic heart valve.

34. The prosthesis of claim 33 wherein the prosthetic heart valve is a stentless valve with flexible leaflets and a leaflet support structure that is positioned to avoid blockage of the tubules.

35. The prosthesis of claim 30 wherein the biocompatible material comprises tissue.

36. A prosthesis comprising:
    biocompatible material formed into a generally cylindrical section having a generally straight surface in an axial direction and an integral expanded section connected to the generally cylindrical section to form a conduit with a lumen extending through the generally cylindrical section and the expanded section, the free edge of the expanded section having scallops that fit adjacent to and downstream from the commissures of a native heart valve.

37. The prosthesis of claim 36 wherein the biocompatible material comprises tissue.

38. The prosthesis of claim 36 further comprising a prosthetic valve attached to the biocompatible material.

39. A prosthesis comprising:
a reinforcement element,
a prosthetic conduit comprising biocompatible material with a generally straight surface in an axial direction and
a prosthetic valve attached to the prosthetic conduit,
wherein the reinforcement element comprises a circular band that is circumferentially attached proximate one end of the prosthetic conduit downstream from the prosthetic valve to inhibit dilation of the conduit and to promote proper valve function.

40. The prosthesis of claim 39 wherein the prosthesis further comprises a reinforcement near the inflow edge.

41. A prosthesis comprising
a reinforcement element,
a prosthetic conduit comprising biocompatible material and
a prosthetic valve attached to the prosthetic conduit,
wherein the reinforcement element is circumferentially attached proximate one end of the prosthetic conduit downstream from the prosthetic valve to inhibit dilation of the conduit and to promote proper valve function,
wherein the prosthetic conduit comprises a generally cylindrical section having a generally straight surface in an axial direction and an expanded section extending from the generally cylindrical section, wherein the reinforcement element is positioned at the junction between the generally cylindrical section and the expanded section.

42. A prosthesis comprising
a first prosthetic conduit section of a conduit, the first prosthetic conduit section having a generally straight surface in an axial direction and
a second integral prosthetic conduit section of a conduit, wherein an inflow edge of the first prosthetic conduit section is configured for attachment to an outflow edge of the second prosthetic conduit section, the first prosthetic conduit section having a generally cylindrical section and the second prosthetic conduit section comprising a prosthetic valve, and
a reinforcement element including a circular band on the conduit that limits dilation of the conduit.

43. The prosthesis of claim 42 wherein the second conduit section has an expanded section having a maximum diameter at least about 10% greater than the average diameter of the generally cylindrical section.

44. The prosthesis of claim 42 wherein the prosthetic valve is a mechanical valve.

45. The prosthesis of claim 44 wherein the second conduit section has an expanded section with a generally spherical shape over a portion of a sphere.

46. The prosthesis of claim 42 wherein the prosthetic valve has flexible leaflets.

47. The prosthesis of claim 46 wherein the second conduit section has an expanded section with three lobes.

48. A prosthesis comprising
a reinforcement element and
a prosthetic conduit comprising biocompatible material, the conduit having a generally straight surface in an axial direction and being shaped for attachment around a heart valve,
wherein the reinforcement element comprises a band circumferentially attached to the prosthetic conduit proximate to the outflow edge to limit dilation.

49. A prosthesis comprising:
a reinforcement element and
a prosthetic conduit comprising biocompatible material, the conduit having a generally straight surface in an axial direction and being shaped for attachment to a valve,
wherein the reinforcement element is circumferentially attached to the prosthetic conduit proximate to the outflow edge,
further comprising a prosthetic valve attached to the prosthetic conduit.

50. A prosthesis comprising:
a reinforcement element,
a prosthetic conduit comprising biocompatible material and having a generally straight surface in an axial direction and
a prosthetic valve circumferentially attached to the prosthetic conduit, wherein the reinforcement element is attached to the prosthetic conduit proximate to the inflow edge.

51. A prosthesis comprising
a reinforcement element and
a prosthetic conduit comprising biocompatible material, the prosthetic conduit having only a single generally cylindrical section that has a generally straight surface in an axial direction and an expanded section extending from an end of the generally cylindrical section,
wherein the reinforcement element is a circumferentially positioned band at the junction between the generally cylindrical section and the expanded section to limit dilation of the junction.

* * * * *